(12) United States Patent
Hastings et al.

(10) Patent No.: US 6,375,609 B1
(45) Date of Patent: Apr. 23, 2002

(54) MICRO-MOTOR ACTUATED THERAPEUTIC DEVICE

(75) Inventors: Roger Hastings; Kenneth Larson, both of Maple Grove; Michael Berman, Golden Valley; Daniel M. Lafontaine, Plymouth, all of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/563,326

(22) Filed: May 3, 2000

Related U.S. Application Data

(63) Continuation of application No. 09/258,361, filed on Feb. 26, 1999, now Pat. No. 6,089,235, which is a division of application No. 08/795,602, filed on Feb. 5, 1997, now Pat. No. 5,823,199, which is a division of application No. 08/343,045, filed on Nov. 21, 1994, now Pat. No. 5,628,719, which is a continuation-in-part of application No. 07/981,612, filed on Nov. 25, 1992, now abandoned.

(51) Int. Cl.[7] .............................................. A61B 19/00
(52) U.S. Cl. ....................................................... 600/104
(58) Field of Search .......................... 128/899; 60/104, 60/106, 115, 116, 137, 183

(56) References Cited

U.S. PATENT DOCUMENTS

| 4,758,222 A | * | 7/1988 | McCoy | 604/95 |
| 5,019,121 A | * | 5/1991 | Krauter | 128/4 |
| 5,406,940 A | * | 4/1995 | Melzer et al. | 128/6 |

* cited by examiner

*Primary Examiner*—William E. Kamm
(74) *Attorney, Agent, or Firm*—Todd P. Messal

(57) ABSTRACT

An in vivo source of mechanical energy is provided in close proximity to its load. In the disclosed embodiments, the mechanical energy source is a miniaturized motor ("micromotor") and the load is a miniaturized perfusion pump located at the distal end of a transluminal catheter. The motor is powerful enough to provide the electrical energy needed by the perfusion pump to fluid, and yet small enough to fit inside a body vessel. A position sensor may be provided for automatically controlling the motor's driving current so that it is corresponds to the applied load. An embodiment of the perfusion pump is also provided in which an external energy source is used. Another embodiment is provided wherein a balloon/pump/miniaturized-motor configuration is provided on a distal end of a catheter.

22 Claims, 17 Drawing Sheets

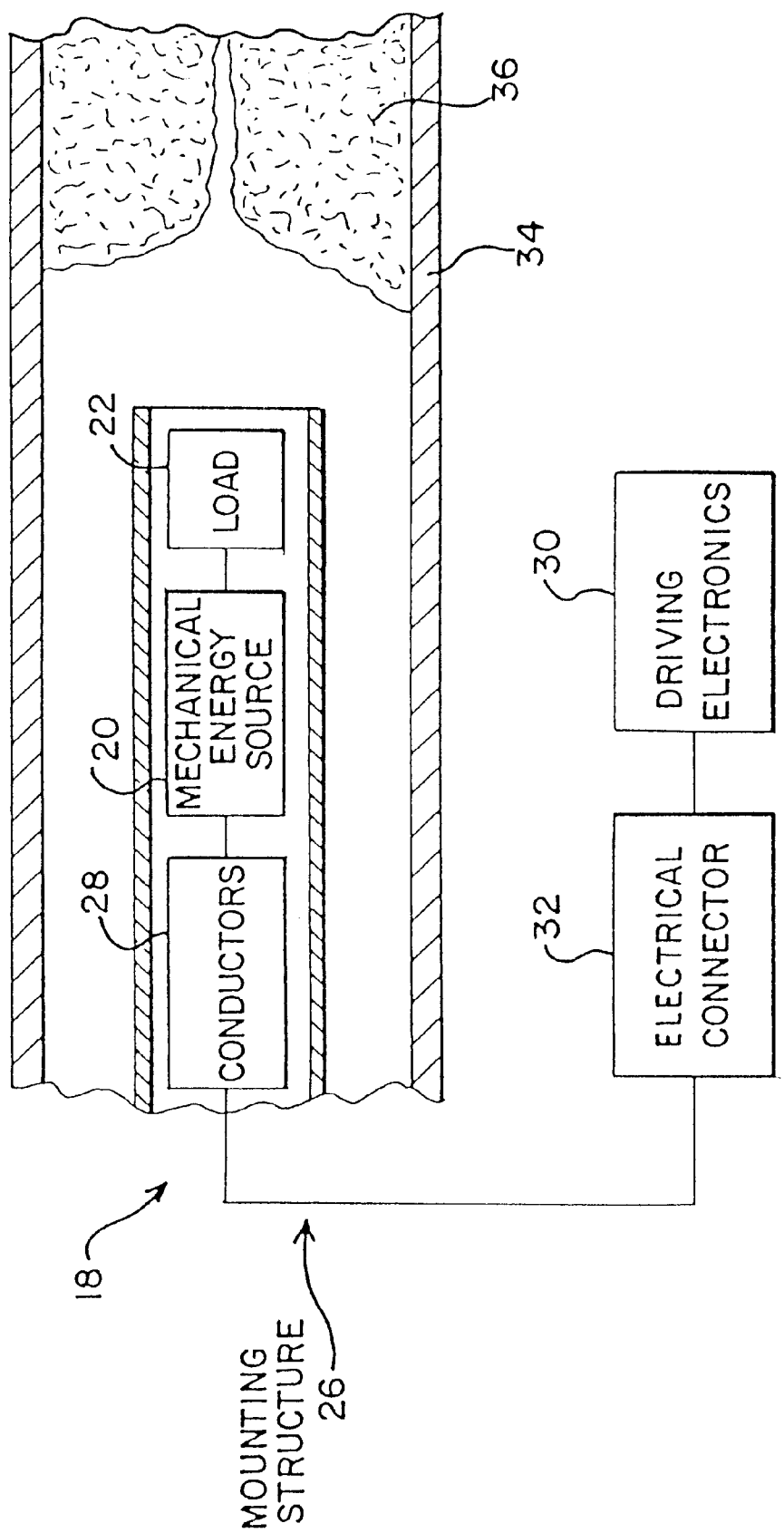

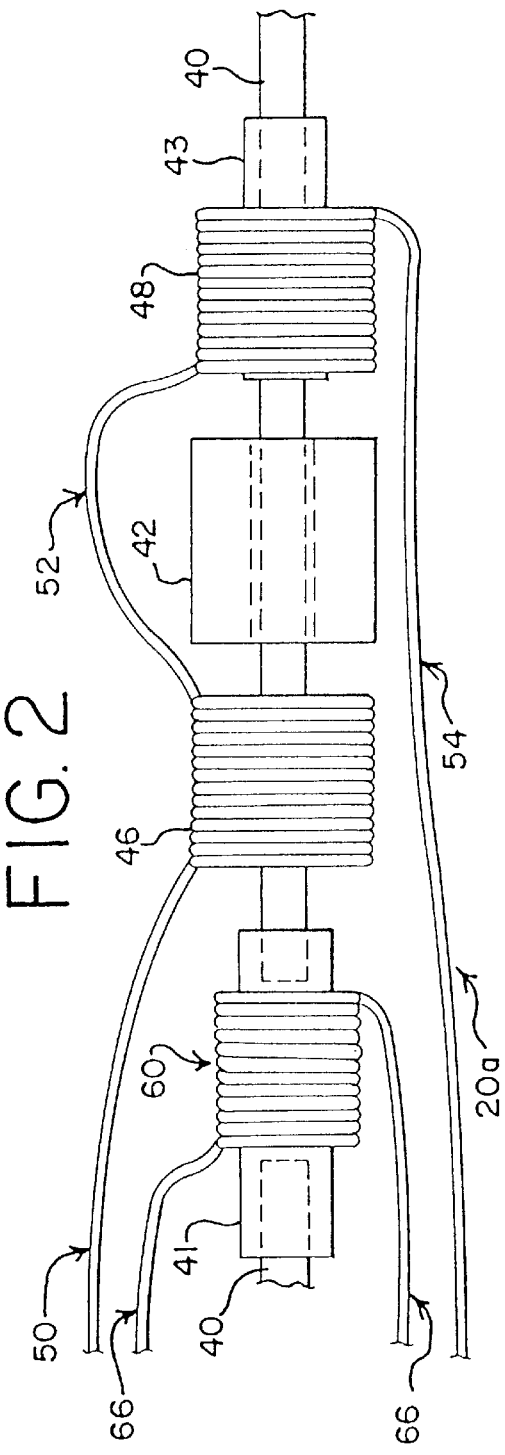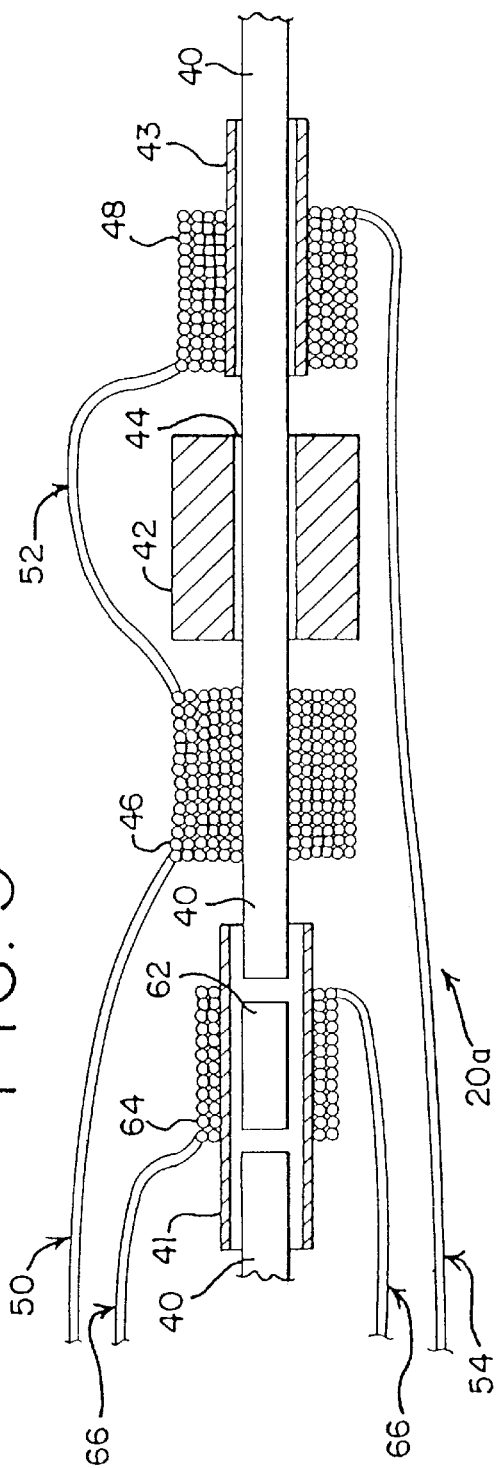

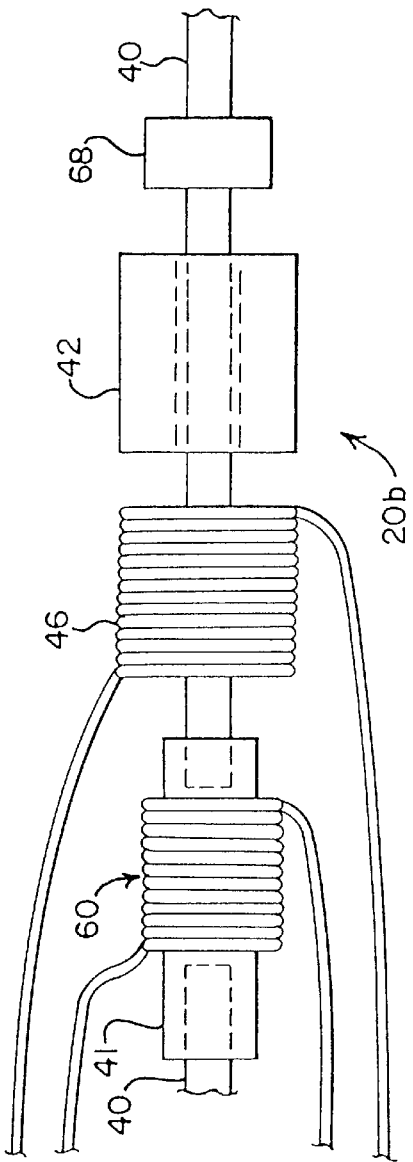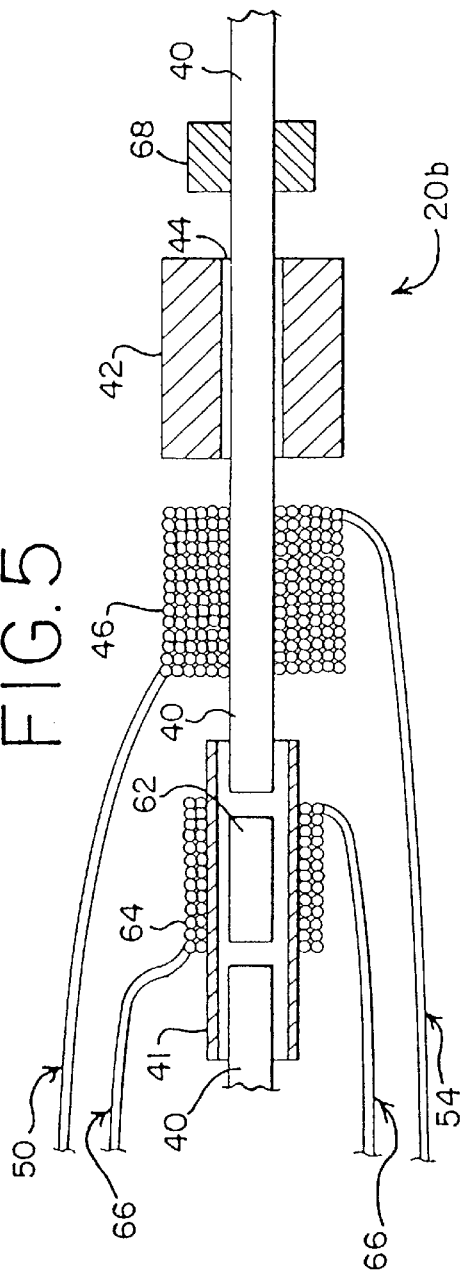

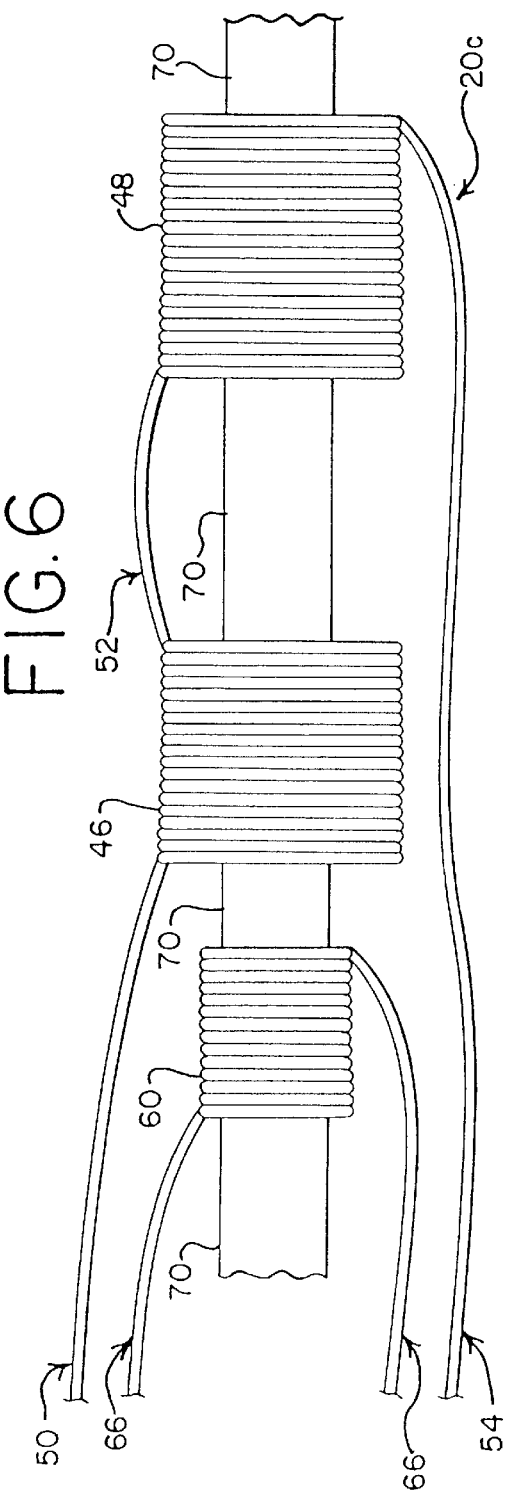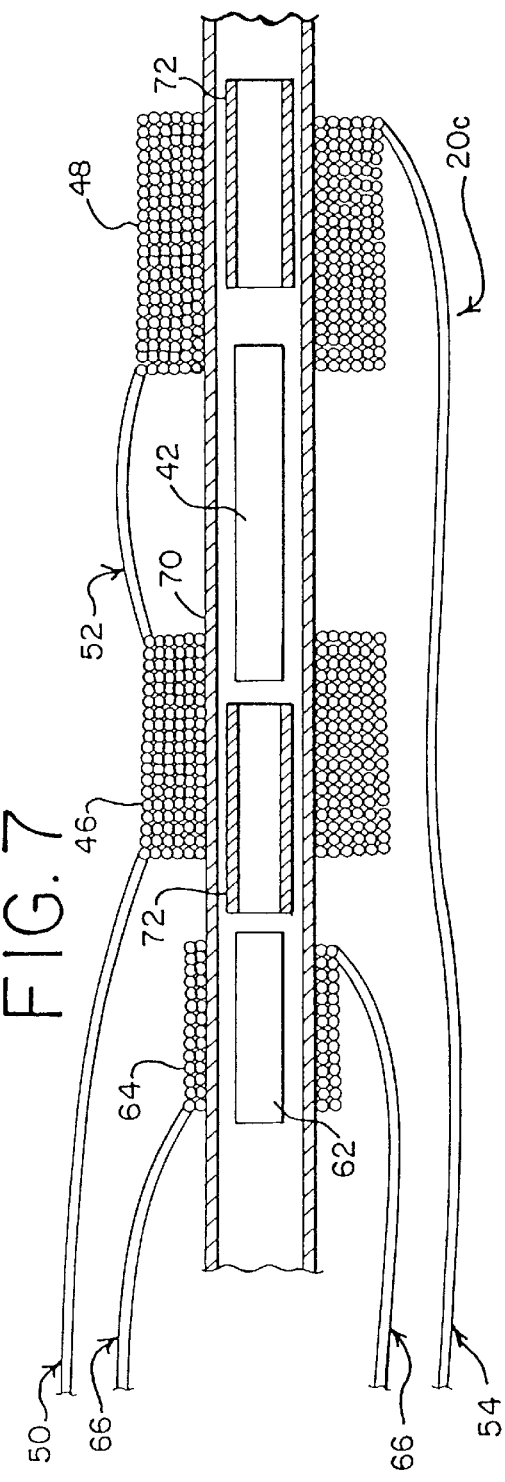

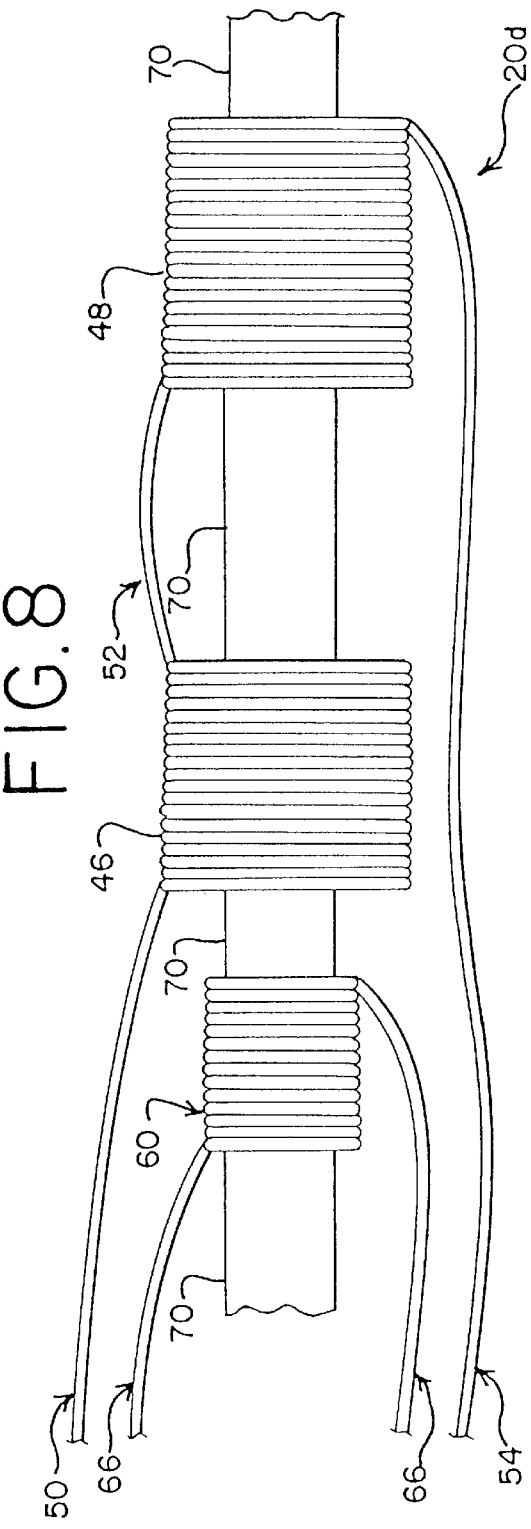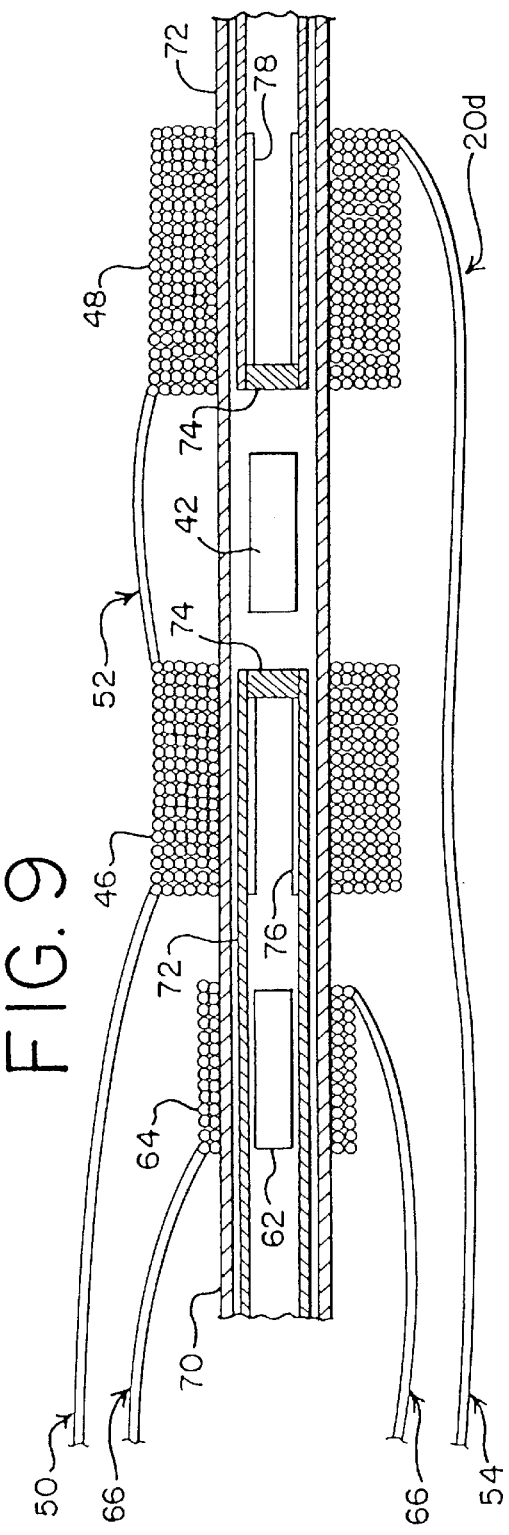

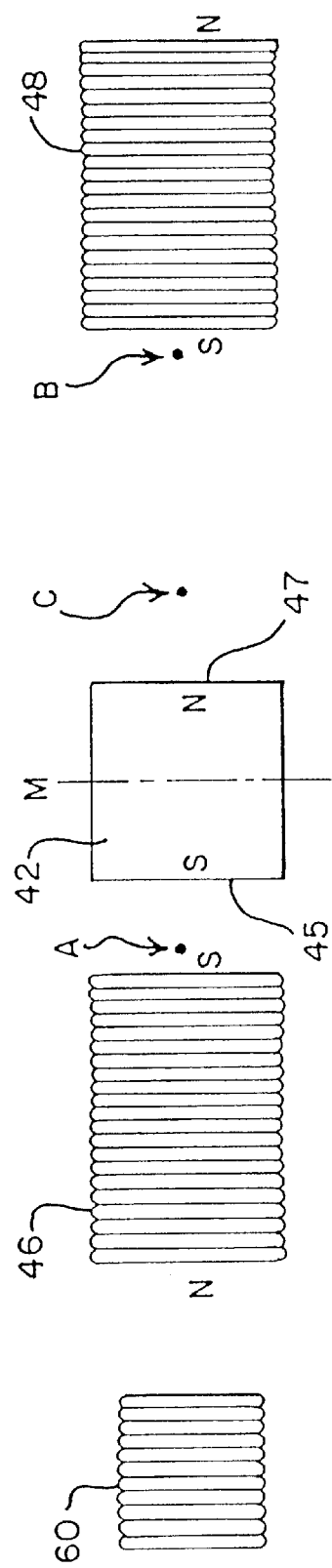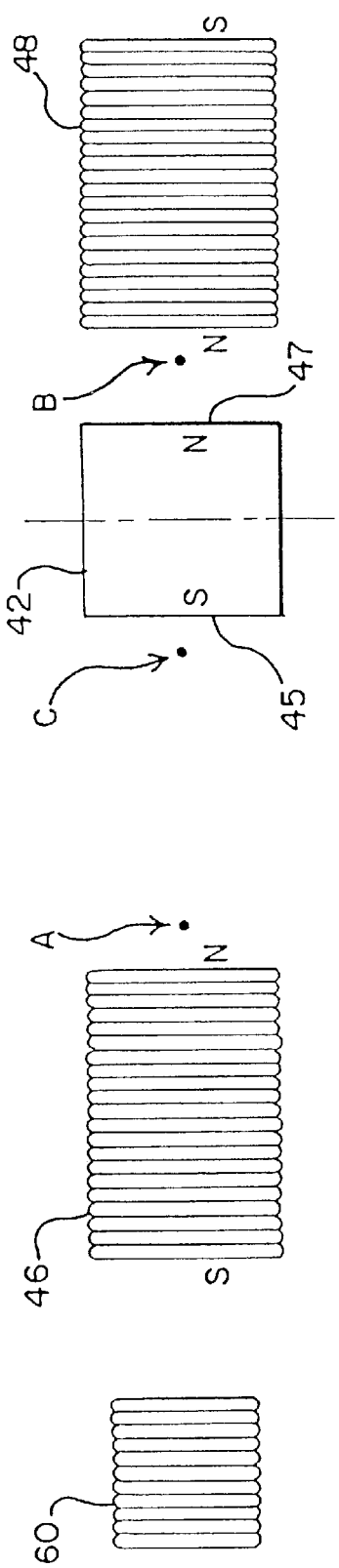

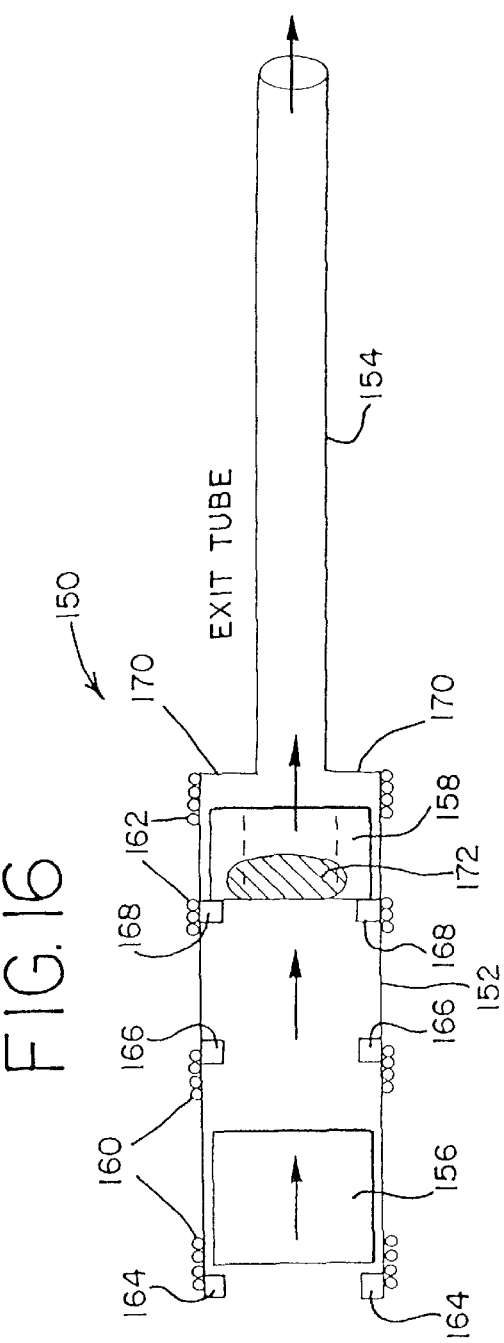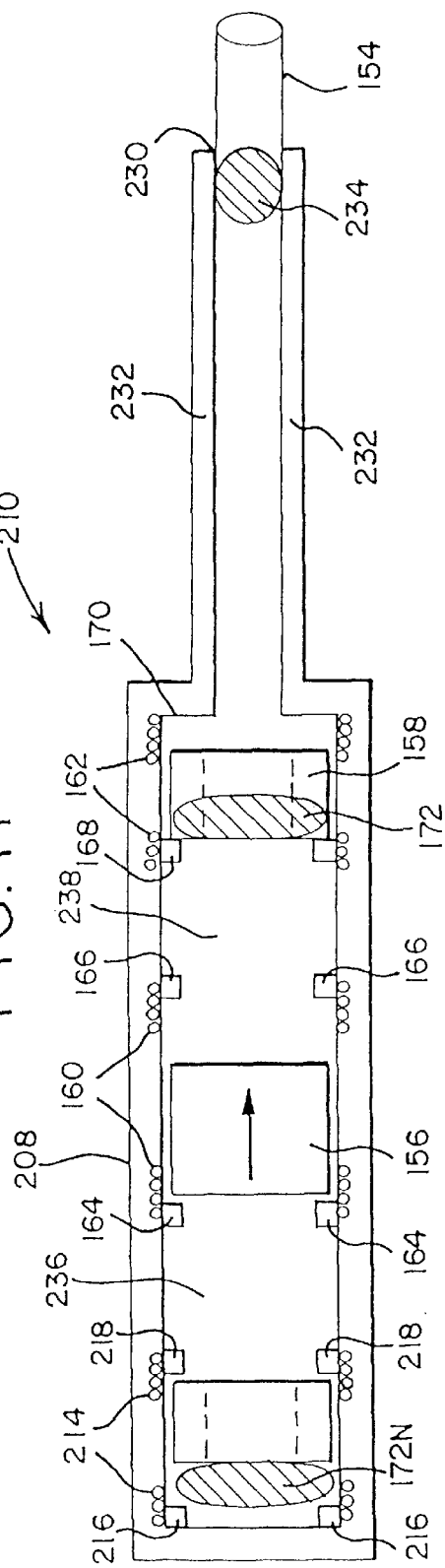

MICRO-MOTOR ACTUATED THERAPEUTIC DEVICE

STATEMENT OF RELATED APPLICATIONS

This is a continuation of application Ser. No. 09/258,361, filed Feb. 26, 1999 (now U.S. Pat. No. 6,089,235), which is a divisional of application Ser. No. 08/795,602, filed Feb. 5, 1997 (now U.S. Pat. No. 5,823,199), which is a division of application Ser. No. 08/343,045 filed Nov. 21, 1994 (now U.S. Pat. No. 5,628,719), which is a continuation-in-part of application Ser. No. 07/981,612, filed Nov. 25, 1992, now abandoned. The entire disclosure of Ser. No. 07/981,612 is incorporated herein by reference.

BACKGROUND OF THE INVENTION

1. Field of the Invention

This invention relates in general to an in vivo mechanical energy source. More particularly, it relates to a miniaturized mechanical motor that is small enough to fit inside a percutaneous transluminal device and yet powerful enough to do work.

2. General Description of the Art

Catheters are used in a variety of percutaneous transluminal treatments, such as coronary, cerebral and peripheral angioplasties. The general objective of these treatments is to open obstructions or lesions within a body vessel such as a blood vessel. For example, in percutaneous transluminal coronary angioplasty (PTCA), a guide catheter is introduced at an appropriate location in the patient's body and routed through the vascular system into the aorta and coronary orifice. A thin and relatively flexible guide wire is advanced through the guide catheter to the arteries, and then steered into side branches (if necessary) to access the obstruction. Once the guide wire has established a path across the obstruction, an "over-the-wire" dilatation balloon catheter is passed over the proximal end of the guide wire until the balloon is adjacent the obstruction. The balloon is then inflated by introducing a fluid into the balloon through an inflation lumen in the catheter. The inflated balloon expands against the blockage to dilate the obstructed blood vessel. Another type of balloon catheter known as "fixed-wire," eliminates the need for a separate guide wire by attaching a short flexible guide wire to the distal end of the catheter.

Other methods of treating blocked blood vessels involve the use of miniaturized mechanical devices to cut, abrade, or otherwise open a passage through the obstruction. For example, U.S. Pat. No. 4,936,845 discloses a catheter having a rotating head at its distal end for boring a passageway through an obstructed blood vessel. U.S. Pat. No. 4,854,325 discloses a guide wire that is mechanically driven through a ramming back-and-forth action to assist in forming a pilot passageway through the obstruction. Other miniaturized mechanical devices are disclosed in U.S. Pat. Nos. 5,007,917; 5,011,490; 5,030,201; and 5,059,203.

The mechanical devices disclosed in the above-identified patents are driven by external motors which are connected to the device through a drive shaft extending along the length of the catheter. There are several problems with transmitting mechanical energy down a relatively long drive shaft in a catheter. For example, the drive shaft dissipates a significant amount of the mechanical energy into the patient's blood vessel. This can cause considerable trauma, and the patient often requires drug treatments to counteract the negative effects. The dissipated mechanical energy also results in large energy losses. Because of the small dimensions of the vascular system, the energy needed at the in vivo work site is typically less than 1 watt. However, due to the tremendous energy losses through the drive shaft, external motors must typically generate about 100 watts in order to produce less than 1 watt at the in vivo work site.

Also, external motors are large and can require complicated connectors for coupling them to the relatively small drive shaft. In addition, drive shafts are relatively rigid, and accordingly, they are difficult to negotiate through the vascular system. Thus, the placement of a drive shaft along the length of a catheter severely compromises the catheter's flexibility.

U.S. Pat. No. 5,176,141 issued to Bom discloses a disposable ultrasonic catheter that has a rotatable acoustic mirror for directing sound waves outwardly into tissue and for receiving echo sounds and directing the echo sounds to a transducer. The transducer's output is transmitted to a visual display which displays an ultrasound picture of the tissue whereby one can determine the makeup of the tissue, e.g., hard or soft. A motor is provided in the catheter for rotating the mirror at selected rpm.

The mirror in Bom is a very tiny and light weight acoustic crystal transducer. The motor that rotates the mirror is illustrated only as a cylinder 3 in FIGS. 1–3 of Bom. Bom provides no details about the construction and operation of its motor, except to describe it as a "multi-polar microsynchronized motor." Bom, col. 4, lines 11–12. Accordingly, the motor disclosed in Bom is not capable of delivering the more than about 0.01 watts of energy that would be needed in order to do any appreciable work such as pumping blood (preferably via a perfusion pump) or operating dottering devices, inflation pumps, atherectomy devices, and other such devices.

Thus, it would be beneficial to provide a mechanical energy source that is powerful enough to do work yet small enough to fit inside a body vessel, thereby allowing the mechanical energy source to be placed inside a percutaneous transluminal device and in close proximity to a load at the distal end of the device.

Thus, it would also be beneficial to provide an in vivo perfusion pump that is specially adapted to be used with an in vivo mechanical energy source, said energy source being powerful enough to do work yet small enough to fit inside a body vessel.

The following terms are used throughout this disclosure and are intended to have the following meanings:

The term "distal" refers to the end of the percutaneous device that is inserted in the patient's vascular system.

The term "proximal" refers to the end of the percutaneous device that is outside the patient's vascular system.

SUMMARY OF THE INVENTION

It is an object of the present invention to provide a method and structure for generating mechanical energy inside the vascular system.

It is also an object of the present invention to provide a method and structure for generating mechanical energy at the distal end of a percutaneous transluminal device.

It is another object of the present invention to provide mechanical energy in close proximity to a miniaturized medical device located at the distal end of a percutaneous transluminal device.

It is yet another object of the present invention to provide a miniaturized mechanical energy source that is powerful enough to do work.

It is yet another object of the present invention to provide an in vivo perfusion pump capable of being used with a miniaturized mechanical energy source that is powerful enough to adequately perfuse a coronary artery.

These and other objects are realized in accordance with the present invention by providing a miniaturized mechanical energy source that is small enough to fit inside a body vessel. The disclosed embodiments of the invention are substantially cylindrical miniaturized motors ("micromotors") that measure less than 250 mils in length and less than 80 mils in diameter. In one embodiment, the motor includes a small cylindrical magnet linearly aligned between two sets of driving coils. Current is applied to the driving coils so that they periodically and alternately repel and attract the magnet, thereby driving it back and forth between the two sets of coils. In an alternative embodiment, a sensor is linearly aligned with the magnet and the driving coils. The sensor detects the relative position of the magnet and then directs an external driving circuit to deliver current to the driving coils based on the magnet's position. The driving coils are connected in series so that the same current flows through both sets of coils.

The disclosed embodiments of the present invention provide several advantages. The sensor delivers current to the driving coils based on the actual position of the magnet, and thus a load placed on the magnet cannot force it out of phase with the driving current. The series connection from one set of driving coils to the other, along with the directions (sense) of the driving coil windings, insures that one set of coils is always repelling the magnet when the other set of coils is attracting it. Additionally, the motor's linear configuration provides optimal coupling between the driving coils and the magnet. This linear configuration also allows the motor to fit conveniently inside a conventional elongated catheter. These and other features allow the present invention to perform work using motors that are small enough to fit inside a conventional transluminal catheter. The disclosed motors are placed in close proximity to their load, and thus they are not burdened by the considerable power losses associated with transmitting mechanical energy down a relatively long drive shaft.

The present invention may thus be utilized to provide efficient, in vivo mechanical energy to a wide range of loads and applications such as perfusion pumps, dottering devices, inflation pumps, atherectomy devices, delivering vibrational energy to relax arterial muscles, and others.

A particularly advantageous application of the micromotors is disclosed in connection with several embodiments of a novel perfusion pump, which may be used with the disclosed in vivo mechanical energy source.

In one embodiment, the perfusion pump includes an external energy source, a push wire having its proximal end connected to the external energy source, a reciprocating piston connected to the distal end of the push wire, an intermediate tubular chamber surrounding the piston, an intake aperture formed in the chamber wall, and a distal exit tube coupled to the chamber. The external energy source reciprocates the push wire, which reciprocates the piston within the intermediate tubular chamber. The piston draws fluid into the intermediate chamber on its backstroke, thereby filling the chamber with fluid when the piston crosses the intake aperture. Fluid is forced out of the exit hole when the piston moves on its forward stroke.

In another embodiment, the perfusion pump includes a tubular chamber, a piston magnet within the chamber, piston winding coils around the tubular chamber, a valve magnet within the chamber, valve winding coils around the tubular chamber, an intake aperture formed in the chamber wall, and a distal exit tube coupled to the chamber. Electrical energy is provided to the piston winding coils to reciprocate the piston within the tubular chamber, thus providing an in vivo mechanical energy Source. Electrical energy is also provided to the valve windings to periodically move the valve magnet so that it either covers or uncovers the intake aperture. The electrical energy is provided to the piston windings and the valve windings approximately 180 degrees out of phase, so that the valve magnet uncovers the intake aperture whenever the piston moves proximally, and the valve covers the intake aperture whenever the piston moves distally. Accordingly, when the piston moves proximally, it draws fluid through the intake aperture, and when the piston moves distally, it expels fluid through the distal exit tube coupled to the chamber.

In yet another embodiment, the perfusion pump is a double acting pump in which fluid is pumped on both the forward and the back stroke of the piston. The pump includes a tubular chamber, a piston magnet within the chamber, piston winding coils around the tubular chamber, a first valve magnet within the chamber, first valve winding coils around the tubular chamber, a first intake aperture formed in the chamber wall near the first valve magnet, a second valve magnet within the chamber, second valve winding coils around the tubular chamber, a second intake aperture formed in the chamber wall near the second valve magnet, and a distal exit tube coupled to the chamber. Electrical energy is provided to the piston winding coils to reciprocate the piston within the tubular chamber, thus providing an in vivo mechanical energy source. Electrical energy is also provided to the first and second valve windings to periodically move the valve magnet so that it either covers or uncovers the intake aperture. The electrical energy is provided to the piston windings and the valve windings such that the valve magnets alternately cover and uncover the intake apertures.

In the double acting embodiment, two of the magnets are in phase with each other but 180° out of phase with the third magnet (i.e., two magnets move forward while the third magnet is moving backwards). Thus, the magnets automatically reciprocate in lock step (with two magnets always 180° out of phase with the third magnet). Accordingly, the pump is capable of pumping fluid on both the forward and back strokes of the piston. On the backstroke, fluid passes over the coil windings, providing fluid cooling, which allows the pump to operate more efficiently and deliver higher output levels.

In yet another embodiment, any one of the above-described pumps can be incorporated into a variety of balloon catheters

BRIEF DESCRIPTION OF THE DRAWINGS

FIG. 1 is a block diagram of a percutaneous transluminal system embodying the features of the present invention. The system includes a percutaneous transluminal device which is shown with its distal end inserted into a patient's vascular system and positioned near an obstruction in a vessel;

FIG. 2 illustrates a miniaturized motor embodying the in vivo mechanical energy source shown in FIG. 1;

FIG. 3 illustrates a partial sectional view of the motor shown in FIG. 2;

FIG. 4 illustrates another miniaturized motor embodying the in vivo mechanical energy source shown in FIG. 1;

FIG. 5 illustrates a partial sectional view of the motor shown in FIG. 4;

FIG. 6 illustrates another miniaturized motor embodying the in vivo mechanical energy source shown in FIG. 1;

FIG. 7 illustrates a partial sectional view of the motor shown in FIG. 6;

FIG. 8 illustrates yet another motor embodying the in vivo mechanical energy source shown in FIG. 1;

FIG. 9 illustrates a partial sectional view of the motor shown in FIG. 8;

FIGS. 10a and 10b illustrates a travel path for the magnets shown in FIGS. 2–9;

FIG. 16 is a generally schematic representation of a single acting perfusion pump embodying features of the present invention;

FIG. 17 is a generally schematic representation of a double acting perfusion pump embodying features of the present invention;

DETAILED DESCRIPTION OF THE PREFERRED EMBODIMENTS

Figure 11A:
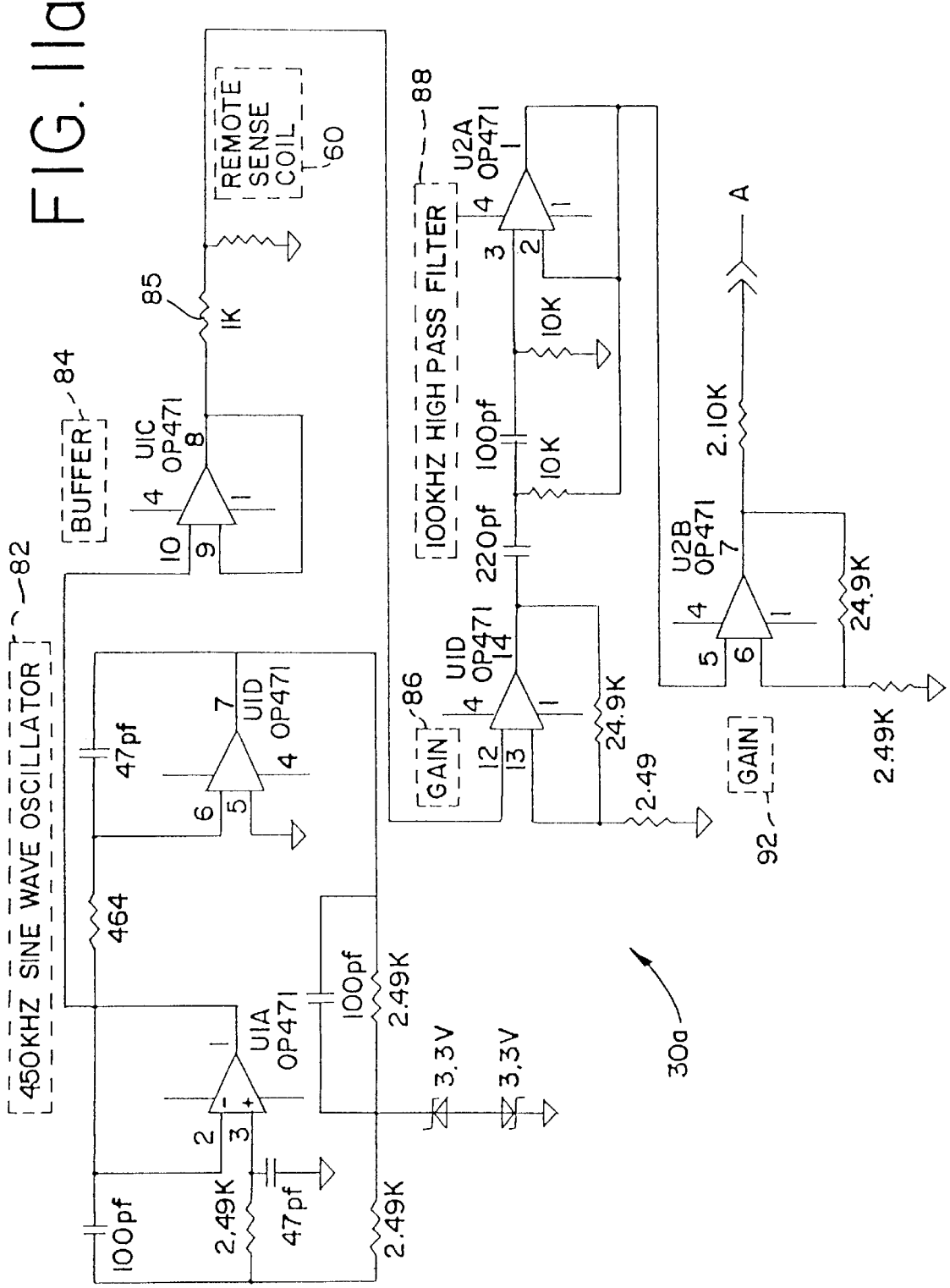
FIGS. 11a and 11b illustrate a schematic diagram of a suitable circuit for implementing the driving electronics shown in FIG. 1.

FIG. 1 is a block diagram of a percutaneous transluminal system 18 embodying features of the present invention. The system 18 generally includes an in vivo mechanical energy source 20; a load 22 mechanically coupled to the mechanical energy source 20; a percutaneous transluminal device 24 for housing the mechanical energy source 20 and the load 22; a mounting structure 26 for mounting the mechanical energy source 20; conductors 28 for carrying current to and from the mechanical energy source 20; driving electronics 30 for sending signals to and receiving signals from the mechanical energy source 20; and an electrical connector 32 for connecting the conductors 28 to the driving electronics 30.

The system 18 is useful in connection with any in vivo vascular therapy involving the use of a motor-driven load 22. For example, in percutaneous transluminal coronary angioplasty (PTCA), an incision is made at an appropriate location in the patient's body, and elongated transluminal devices such as catheters and the like are routed through the patient's vascular system to desired locations therein. PTCA treatments are typically concerned with the removal of vessel obstructions which restrict or block the flow of blood through the vessel. One approach to removing such obstructions is to cut or abrade them using a miniaturized mechanical device at the distal end of a catheter. An example of such an approach is a procedure known as atherectomy, and the medical devices that are used to cut or abrade the vessel obstructions may be referred to generally as atherectomy devices. Other miniaturized medical devices that are used in connection with PTCA and atherectomy related procedures include dottering devices, perfusion pumps and others.

The system 18 shown in FIG. 1 includes an in vivo mechanical energy source 20 for providing mechanical energy to the load 22. As described above, it is contemplated that the load 22 may be any miniaturized medical device that is used in connection with such vascular therapies as PTCA, atherectomy, and others. The mechanical energy source 20 and the load 22 may be mounted to a mounting structure 26 such as a conventional guide wire or a tube. Also, the mechanical energy source 20 and the load 22 are housed within a percutaneous transluminal device such as a conventional tubular catheter 24. An incision is made in the patient at the proper location, and the catheter housing 24 is routed through the patient's vascular system to the obstructed site. The catheter 24 shown in FIG. 1 has been routed through a body vessel 34 to an obstruction 36 therein.

The miniaturized mechanical energy source 20 converts electrical energy into mechanical energy which is then supplied to the load 22. Electrical power is provided to the mechanical energy source 20 by the driving electronics 30. In the disclosed embodiments, the driving electronics 30 is not part of the catheter 24 or the mounting structure 26, and thus it remains external to the patient. It is contemplated, however, that the driving electronics 30 could be implemented as a miniaturized circuit that is also small enough to also fit inside the catheter 24. The driving electronics 30 provides electrical power to the mechanical energy source 20 via an electrical connector 32 and conductors 28. The electrical connector 32 is attached to the proximal end of the catheter 24 via a conventional manifold device (not shown), and the conductors 28 extend along the length of the catheter 24. The electrical connector 32 provides an electrical connection between the conductors 28 and the driving electronics 30.

FIGS. 2 and 3 illustrate a miniaturized motor 20a embodying the in vivo mechanical energy source 20 shown in FIG. 1. The motor 20a is a reciprocating motor that performs work by moving an actuator 42 back and forth. In the disclosed embodiments, the actuator 42 is a magnet 42. The magnet 42 is mechanically coupled to a load 22 (shown in FIG. 1) which can be any miniaturized medical device such as an atherectomy device, a perfusion pump, a dottering device, or others. In its most basic form, the motor 20a includes: a magnet 42 for driving a load 22; proximal and distal driving coils 46, 48 for periodically attracting and repelling the magnet 42 in a prescribed manner; and a mounting structure 26 for securing the relative positions of the motor's components.

The driving electronics 30 (shown in FIG. 1) delivers driving current to the driving coils 46, 48 to thereby establish the polarities of both sets of coils 46, 48. The driving current may be a square wave which periodically changes the polarities of the driving coils 46, 48 so that they periodically attract and repel the magnet 42. For the basic magnet-coil design, the driving electronics 30 may be implemented as a conventional signal generator.

A sensor 60 may also be provided for detecting the relative position of the magnet 42 and controlling the current supplied to the driving coils 46, 48 by the driving electronics 30. The sensor 60 is an inductive device made from a wire coil 64 wound around a metglass core 62. The sensor 60 is positioned close enough to the magnet 42 to partially saturate the metglass core 62. Thus, as the magnet 42 moves closer to the sensor 60, the metglass core 62 is driven closer to saturation. As the magnet 42 moves away from the sensor 60, the metglass core 62 becomes less saturated. Consequently, the electrical inductance of the sensor coils 64 varies, and its value corresponds to the position of the magnet 42 with respect to the sensor 60. Thus, the sensor 60 "senses" the relative position of the magnet 42. The sensor inductance is measured by applying an AC current to the sensor coils 62 and measuring the AC voltage amplitude across the coils 62 The amplitude of this voltage varies in relation to the sensor inductance which varies in relation to the position of the magnet 42.

The voltage across the sensor 60 is detected by the driving electronics 30 via the conductors 28 and the electrical connector 32. The conductors 28 extend along the length of the catheter housing 24, and the electrical connector 32 is attached at the distal end of the catheter housing 24 and/or the mounting structure 26. The electrical connector 32 provides a convenient access point for making the necessary electrical connections between the conductors 28 and the driving electronics 30.

When the sensor 60 is added to the basic magnet-coil design, the conventional signal generator described above is no longer required or used Thus, for the sensor-based design the driving electronics 30 is configured to deliver current to the driving coils 46, 48 based on the position of the magnet 42 as detected by the sensor 60. FIGS. 10a and 10b illustrate the periodic travel path of the magnet 42. The driving coils 46, 48 propel the magnet 42 back and forth along a linear path defined by an extreme proximal point "A", an extreme distal point "B" and a center point "C". When the center line "M" of the magnet 42 is positioned proximally of the center point C, as shown in FIG. 10a, the current from the driving electronics 30 establishes the polarities of the driving coils 46, 48 such that the distal driving coils 48 are attracting the magnet 42 and the proximal driving coils 46 are repelling the magnet 42. When the center line M of the magnet 42 is positioned distally of the center point C, as shown in FIG. 10b, the current from the driving electronics 30 establish the polarities of the driving coils 46, 48 such that the distal coils 48 are repelling the magnet 42 and the proximal coils 46 are attracting the magnet 42. The driving coils 46, 48 are wound in opposite directions and connected in series so that one set of coils will always have the opposite polarity of the other set of coils. This insures that one set of coils is attracting the magnet 42 when the other set of coils is repelling the magnet 42.

Thus, the sensor 60 controls the current applied to the driving coils 48, 46 so that this current is always based on the actual position of the magnet 42. Accordingly, the current applied to the driving coils 46, 48 is always in phase with the position of the magnet 42, even after the load 22 is coupled to the magnet 42. In other words, the driving coils 46, 48 always have the proper attraction and repulsion even if the applied load 22 slows the magnet 42 down. Also, the series connection between the driving coils 46, 48 insures that the same current passes through both sets of coils 46, 48. The coupling between the magnet 42 and the driving coils 46, 48 is enhanced due to the linear alignment of the driving coils 46, 48 and the magnet 42. The linear configuration of the motor 20a also allows it to be placed in the distal end of a tubular catheter 24 and mounted to a small elongated mounting structure 26 such as a guide wire or a small tube.

As shown in FIGS. 2 and 3, a motor 20a embodying the in vivo mechanical energy source 20 (shown in FIG. 1) is mounted linearly on a mounting structure 26 which, in the disclosed embodiment, is a 13 mils OD (outer diameter) NiTi (non-magnetic) guide wire 40, a 14 mils ID (inner diameter)×16 mils OD polyimide tube 41, and another 14 mils ID×16 mils OD polyimide tube 43. The sensor element 60 is made from a 1.2 mils OD insulated wire wound into a sixty-turn set of coils 64 around a metglass core 62 measuring 13 mils×100 mils. The metglass core 62 is positioned inside tube 41 and centered under the sensor coils 64. Thus, the core 62 interrupts the wire 40 so that the wire 40 is provided in two parts coupled together by tube 41. Tube 41 is disposed between the sensor coils 64 and the metglass core 62. The proximal driving coils 48 are made from a 1.2 mils OD insulated wire wound into a sixty turns and eleven layers around the wire 40. The distal driving coils 48 are made from a 1.2 mils OD insulated wire wound into a sixty turns and eleven layers around tube 43. The tubes 41, 43 allow the sensor 60 and the distal driving coils 48 to be moved along the wire 40 to achieve the desired spacings between the motor's components.

The magnet 42 is substantially cylindrical and measures approximately 75 mils in length and 48 mils in diameter. An aperture 44 extends axially through the length of the magnet 42, and the NiTi guide wire 40 extends through the aperture 44. Because the distal driving coils 48 are wound around tube 43, the coils 48 are wound into fewer layers than the proximal driving coils 46 in order to maintain a uniform OD for the motor 20a. The sensor coils 64 are connected to the driving electronics 30 by a set of leads 66. The driving coils 46, 48 are connected to the driving electronics 30 and to each other by a set of leads 50, 52, 54.

FIGS. 4 and 5 illustrate another miniaturized motor 20b embodying the in vivo mechanical energy source 20 shown in FIG. 1. Motor 20b is similar to the motor 20a shown in FIGS. 2 and 3 and described above, except that motor 20b has one set of driving coils 46 located proximally from its reciprocating magnet 42. Motor 20b is mounted linearly on a mounting structure 26 which, in the disclosed embodiment, is a 13 mils OD NiTi guide wire 40 and a 14 mils ID×16 mils OD polyimide tube 41. The sensor 60 is made from a 1.2 mils OD insulated wire wound into a sixty-turn coil 64 around a metglass core 62 measuring 13 mils×100 mils. The metglass core 62 is positioned inside the tube 41 and centered under the sensor coils 64. Thus, the core 62 interrupts the wire 40 so that the wire 40 is provided in two parts coupled together by the tube 41. The tube 41 is disposed between the sensor coils 64 and the metglass core 62. The tube 41 allows the sensor 60 to be moved linearly in relation to the magnet 42 by moving the tube 41 along the guide wire 40. The driving coils 46 are made from a 1.2 mils OD insulated wire wound into sixty turns and eleven layers around the wire 40.

The magnet 42 is substantially cylindrical and measures approximately 75 mils in length and 48 mils in diameter. An aperture 44 extends axially through the length of the magnet 42, and the NiTi guide wire 40 extends through the aperture 44. A heat shrink tube 68 is attached at the distal end of the guide wire 40 for limiting the distal movement of the magnet 42 and defining the total horizontal distance traveled by the magnet 42 during its back-and-forth movement. The sensor coils 64 are connected to the driving electronics 30 by a set of leads 66, and the driving coils 46 are connected to the driving electronics 30 by a set of leads 50, 54.

The motor 20b shown in FIGS. 4 and 5 operates essentially the same as the motor 20a shown in FIGS. 2 and 3. The sensor 60 is an inductive device that senses the position of the magnet 42 by developing a voltage corresponding to the relative position of the magnet 42. The driving electronics 30 detects the voltage across the sensor 60 and outputs a driving current to the driving coils 46 based on this voltage. When the center line M of the magnet 42 is proximal of the center point C (shown in FIG. 10a), the current from the driving electronics 30 establishes a polarity in the driving coils 46 such that they repel the magnet 42. When the center line M of the magnet 42 is distal of the center point C (shown in FIG. 10b), the current from the driving electronics 30 establishes a polarity in the driving coils 46 such that they attract the magnet 42. The heat shrink tube 68 at the distal end of the wire 40 limits the magnet's movement away from the driving coils 46.

FIGS. 6 and 7 illustrate another miniaturized motor 20c embodying the in vivo mechanical energy source 20 shown in FIG. 1. Motor 20c includes essentially the same components as the motors 20a and 20b shown in FIGS. 2–5, respectively. However, these components have a slightly different configuration in motor 20c.

The distal and proximal driving coils 46, 48 of motor 20c are positioned around the outer perimeter of the reciprocating magnet 42. The motor 20c is housed at the distal end of a polyimide tube 70. The magnet 42 is positioned within the tube 70, and the driving coils 46, 48 are wound around the tube 70 as shown in FIGS. 6 and 7. Additional polyimide tubes 72 are provided at each end of the magnet 42 to define the linear travel (displacement) of the magnet 42. The proximal and distal driving coils 46, 48 are each made from a 1.2 mils OD insulated wire wound into sixty turns and eleven layers around the polyimide tube 70. The magnet 42 is substantially cylindrical and measures approximately 200 mils in length and 48 mils in diameter. The sensor 60 shown in FIGS. 6 and 7 is identical to the sensor 60 shown in FIGS. 2–5. The sensor coils 64 are connected to the driving electronics 30 by a set of leads 66. The proximal and distal driving coils 46, 48 are connected to the driving electronics 30 and to each other by a set of leads 50, 52, 54.

Although they are configured somewhat differently, the sensor 60, driving coils 46, 48 and reciprocating magnet 42 of motor 20c operate in substantially the same manner as the motors 20a and 20b shown in FIGS. 2–5. The sensor 60 is an inductive device that senses the position of the magnet 42 by developing a voltage corresponding to the relative position of the magnet 42. The driving electronics 30 detects the voltage across the sensor 60 and outputs a driving current to the driving coils 46, 48 based on this voltage. When the center line M of the magnet 42 is proximal of the center point C (shown in FIG. 10a), the current from the driving electronics 30 establishes the polarities of the driving coils 46, 48 such that the proximal coils 46 repel the magnet 42 and the distal coils 48 attract the magnet 42. When the center line M of the magnet 42 is distal of the center point C (shown in FIG. 10b), the current from the driving electronics 30 establishes the polarities of the driving coils 46, 48 such that the proximal coils 46 attract the magnet and the distal coils repel the magnet 42.

FIGS. 8 and 9 illustrate another miniaturized motor 20d embodying the in vivo mechanical energy source 20 shown in FIG. 1. Motor 20d utilizes approximately the same components and configuration as the motor 20c shown in FIGS. 6 and 7. Motor 20d is housed at the distal end of a polyimide tube 70. The magnet 42 is positioned within the tube 70, and the driving coils 46, 48 are wound around the tube 70 as shown in FIGS. 8 and 9. Additional polyimide tubes 72 are provided at each end of the magnet 42 to act as "stops" and to define the magnet's linear path.

Motor 20d is different from motor 20c in that the tubes 72 include an epoxy filling 74 which limits the magnet's linear travel distance (displacement). Motor 20d also provides permeable FeNiCo cores 76, 78 inside each of the driving coils 46, 48. The permeable cores 76, 78 inside the driving coils 46, 48 provide the magnetic attraction that moves the magnet 42 back and forth. For motor 20d, the driving electronics 30 provide pulsed currents (shown in FIG. 14) to the driving coils 46, 48 rather than the square-wave currents (shown in FIG. 13) utilized in connection with the earlier embodiments. This will be discussed in more detail later in this disclosure under the detailed description of the driving electronics 30. The epoxy 74 also acts as a spacer to prevent the magnet 42 from magnetically sticking to the cores 76, 78 during the magnet's back and forth movement.

The sensor 60 associated with motor 20d operates in substantially the same manner as the sensor 60 associated with the motors 20a, 20b, 20c shown in FIGS. 2–7. The is sensor 60 is an inductive device that senses the position of the magnet 42 by developing a voltage corresponding to the relative position of the magnet 42. The driving electronics 30 detects the voltage across the sensor 60 and outputs a driving current to the driving coils 46, 48 based on this voltage.

Figure 14:
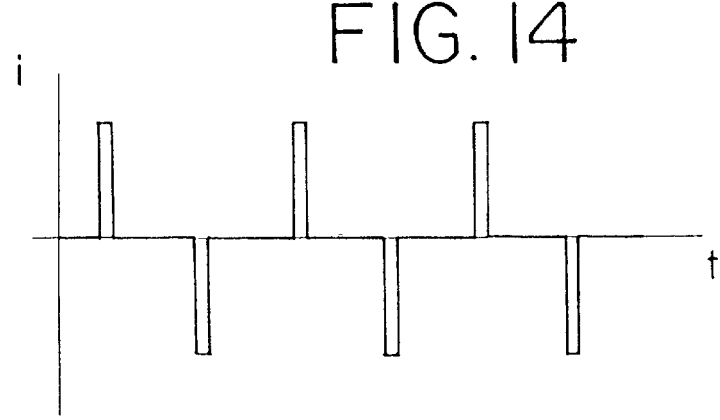
FIG. 14 illustrates a wave-form of the current applied to the driving coils shown in FIGS. 8 and 9.

The driving current associated with motor 20d is a pulsed current as shown in FIG. 14. Like the previous embodiments, the driving current alters the polarities of the driving coils 46, 48 so that they alternately repel and attract the magnet 42. However, for motor 20d, the major attraction forces are supplied by the cores 76, 78, and the driving current supplies the force to launch the magnet 42 away from one core, 76 or 78, so that it can come under the influence of the other core. When the proximal end 45 of the magnet 42 is close to core 76, a pulse of current is provided from the driving electronics 30 to establish a polarity in coils 46 such that they repel the magnet 42 with sufficient force to overcome the attraction of core 76 and propel the magnet 42 away from core 76. When the distal end 47 of the magnet 42 is close to core 78, a pulse of current is provided from the driving electronics 30 to establish a polarity in coils 48 such that they repel the magnet 42 with sufficient force to overcome the attraction of core 78 and propel the magnet 42 away from core 78.

Motors 20c and 20d provide several advantages. The magnets 42 in these embodiments do not require an aperture for mounting, and thus, manufacturing costs are reduced and increased forces may be achieved. Also, the solid magnet is easier to manufacture. In addition, the solid magnet provides more surface area at the ends of the magnet for coupling to the load 22.

FIGS. 11a, 11b, 12a, 12b and 12c are schematic diagrams of suitable circuits for implementing the driving electronics 30 shown in FIG. 1. A variety of schemes are possible for implementing the general functions of the driving electronics 30 described in this disclosure and these general functions are part of the present invention. However, the details of the particular structure that is chosen to implement these functions are not essential to the invention. Consequently, the circuit details disclosed herein are provided as examples.

Figure 11B:
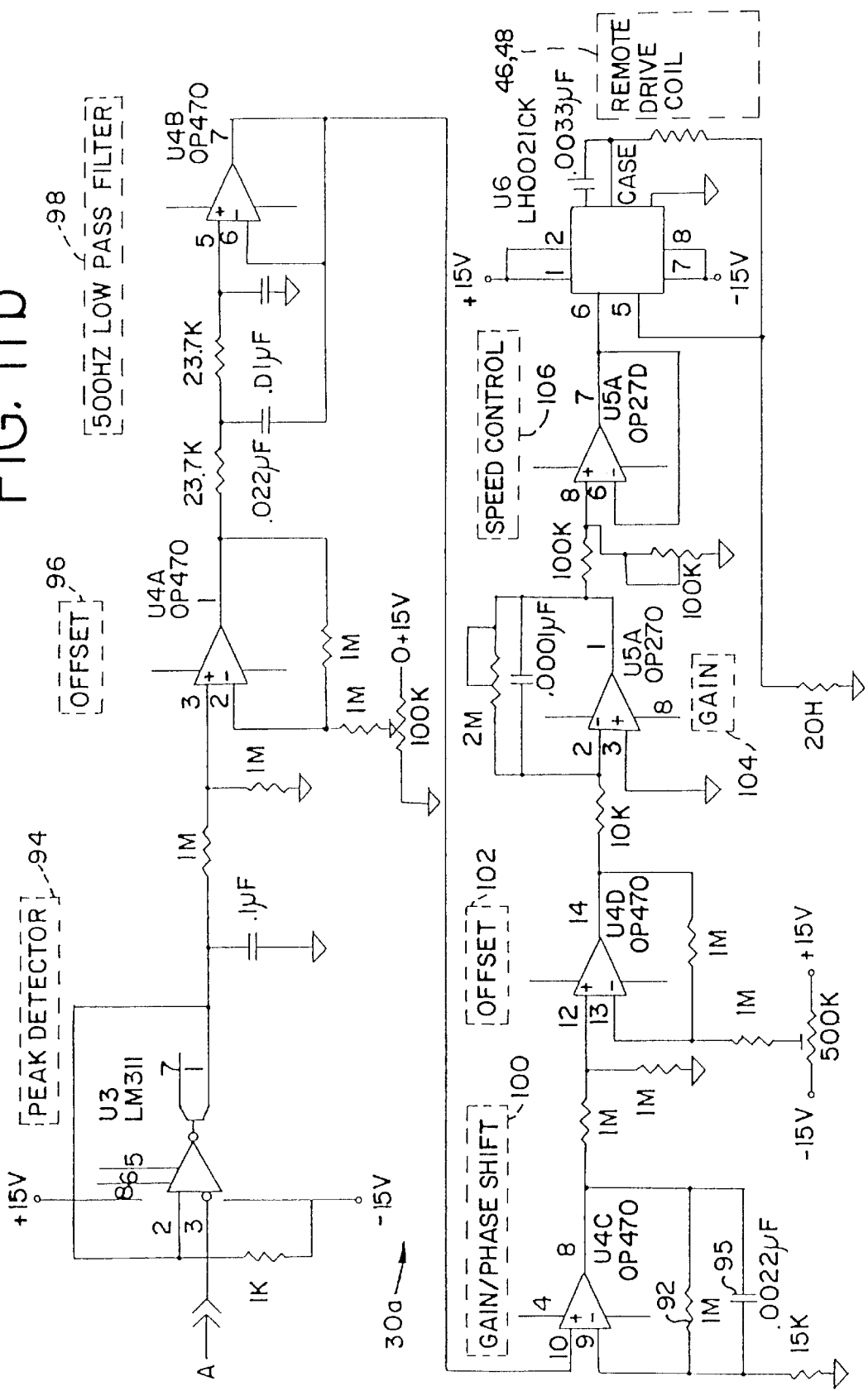

FIGS. 11a and 11b are schematic diagrams of a suitable circuit 30a for implementing the driving electronics 30 shown in FIG. 1. As seen in FIG. 11a, circuit 30a includes a conventional oscillator 82 which applies a 450 kHz sine wave through a buffer driver 84 and a resistor 85 to the sensor 60. The amplitude of the voltage across the sensor 60 varies as the position of the magnet 42 varies. The voltage across the sensor 60 is detected by the driving circuit 30*a* via leads 66 (shown in FIGS. 2–9) and applied to a gain stage 86 having a gain of approximately 30. The output of gain stage 86 is applied to a high pass filter 88 which is set below the oscillator frequency at 100 kHz. The high pass filter 88 eliminates any DC noise levels generated in the conductors 28.

Another gain stage 92 having a gain of approximately 10 is applied to the signal output from the high pass filter 88 and fed into a peak detect circuit 94. The peak detect circuit 94 measures the amplitude of 450 kHz envelope from gain stage 92 and outputs a sine wave having an amplitude that corresponds to the proximity of the magnet 42 to the sensor 60. Also, the frequency of the signal from the peak detect circuit 94 corresponds to the period of the magnet's back and forth movements. For the disclosed embodiments, the frequency of the sine wave output from the peak detect circuit is in the range from about 5 to about 500 Hertz.

The peak detect output is applied to an offset circuit 96 to center the signal around zero. The signal is then applied to a low pass filter 98 (set at approximately 1 kHz). The output from low pass filter 98 is fed to a gain/phase shift circuit 100. Gain/phase shift circuit 100 includes a capacitor 95 in parallel with a gain resistor 92. When the magnet 42 crosses the center point C (see FIGS. 10*a* and 10*b*), the polarities of the driving coils 46, 48 are switched by the driving electronics 30*a*. This switching point (center point C) is controlled by adjusting the value of capacitor 95. If the load 22 is concentrated on one side of the magnet 42, it may be advantageous to establish the switching point closer to the load 22.

The signal output from gain/phase shift circuit 100 is applied to another offset 102 and a variable gain 104. By now, the repeated gain stages have squared the signal so that the signal output from the variable gain 104 is a square wave. The square wave is fed through a speed control circuit 106 to the driving coils 46, 48 via leads 50, 52 and 54 (shown in FIGS. 2–9). The speed control circuit 106 controls the speed or frequency of the magnet 42 by controlling the amplitude of the square wave (shown in FIG. 13).

Figure 13:
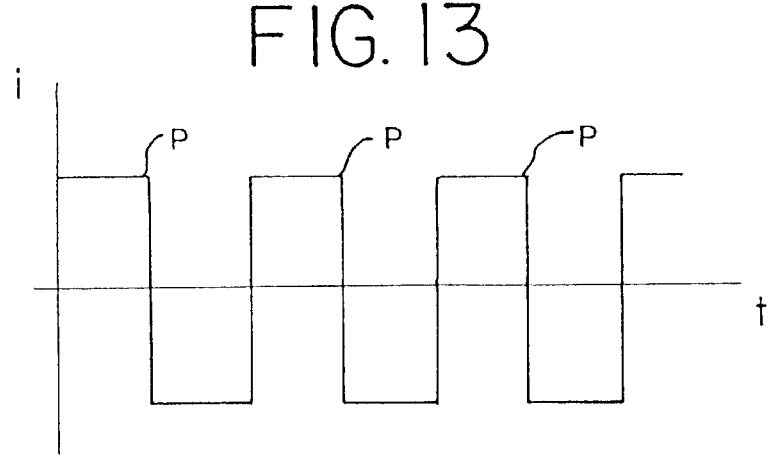
FIG. 13 illustrates a wave-form of the current applied to the driving coils shown in FIGS. 2–7.

FIG. 13 is a wave-form illustrating the current that is output by the driving circuit 30*a* and applied to the driving coils 46, 48. As described herein and shown in FIG. 13, the driving circuit 30*a* periodically switches the current from negative to positive based on the voltage developed across the sensor 60. This voltage is induced by the magnetic flux from the magnet 42 and varies as the position of the magnet 42 changes. When the center line M of the magnet 42 is distal of the center point C (shown in FIGS. 10*a* and 10*b*), the driving circuit 30*a* supplies a positive current to the driving coils 46, 48, and, accordingly, the distal driving coils 48 repel the magnet 42 while the proximal driving coils 46 attract the magnet 42. This produces a net force that moves the magnet 42 away from the distal driving coils 48. When the magnet 42 is proximal of the center point C, the driving circuit 30*a* switches the current supplied to the driving coils 46, 48 to negative as shown at points P in FIG. 13. Accordingly, the polarities of the driving coils are also switched such that the distal driving coils 48 attract the magnet 42 and the proximal driving coils 46 repel the magnet 42. This produces a net force that moves the magnet away from the proximal driving coils 46.

Figure 12A:
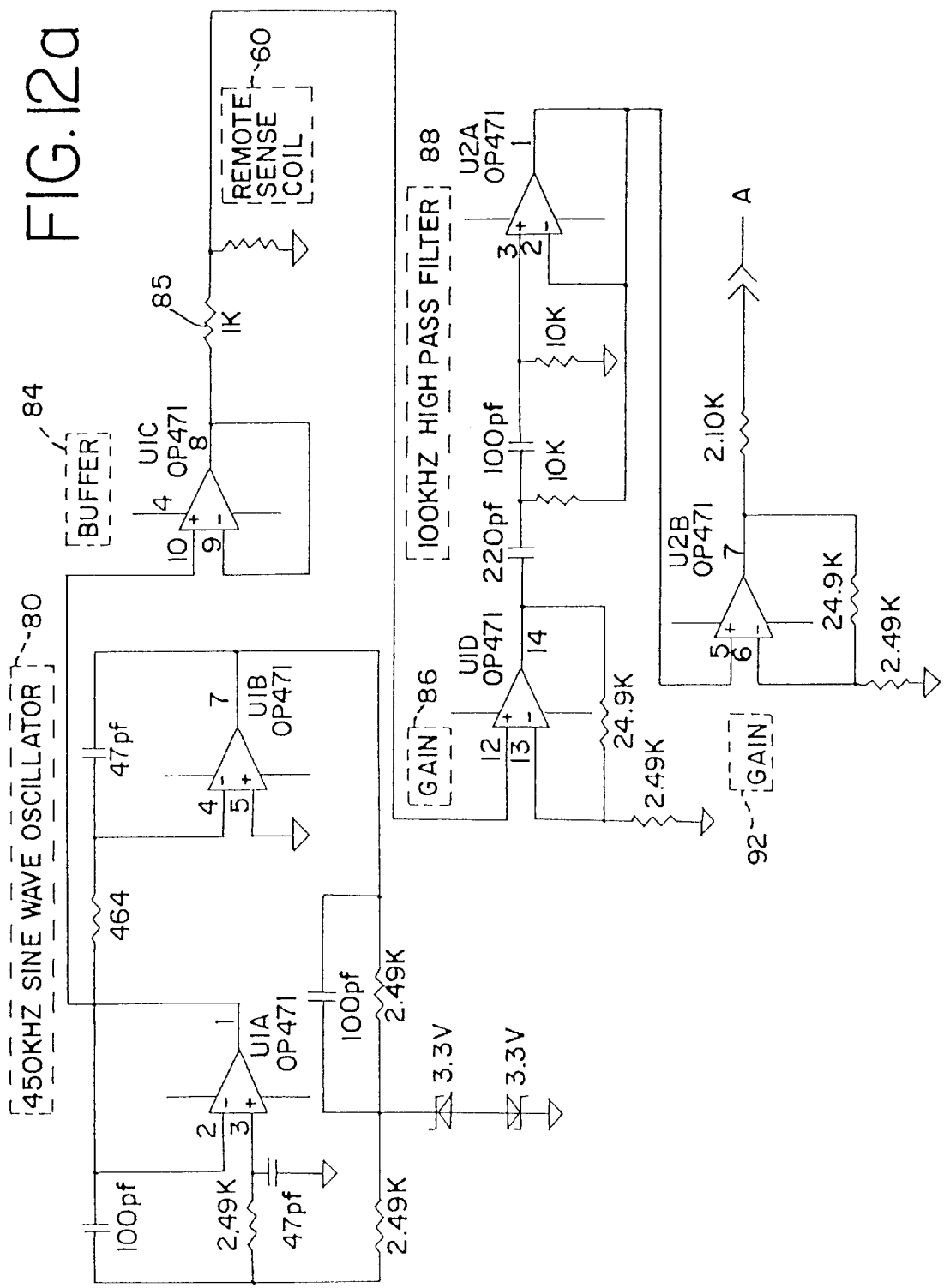
FIGS. 12a, 12b and 12c illustrate a schematic diagram of another suitable circuit for implementing the driving electronics shown in FIG. 1.
Figure 12B:
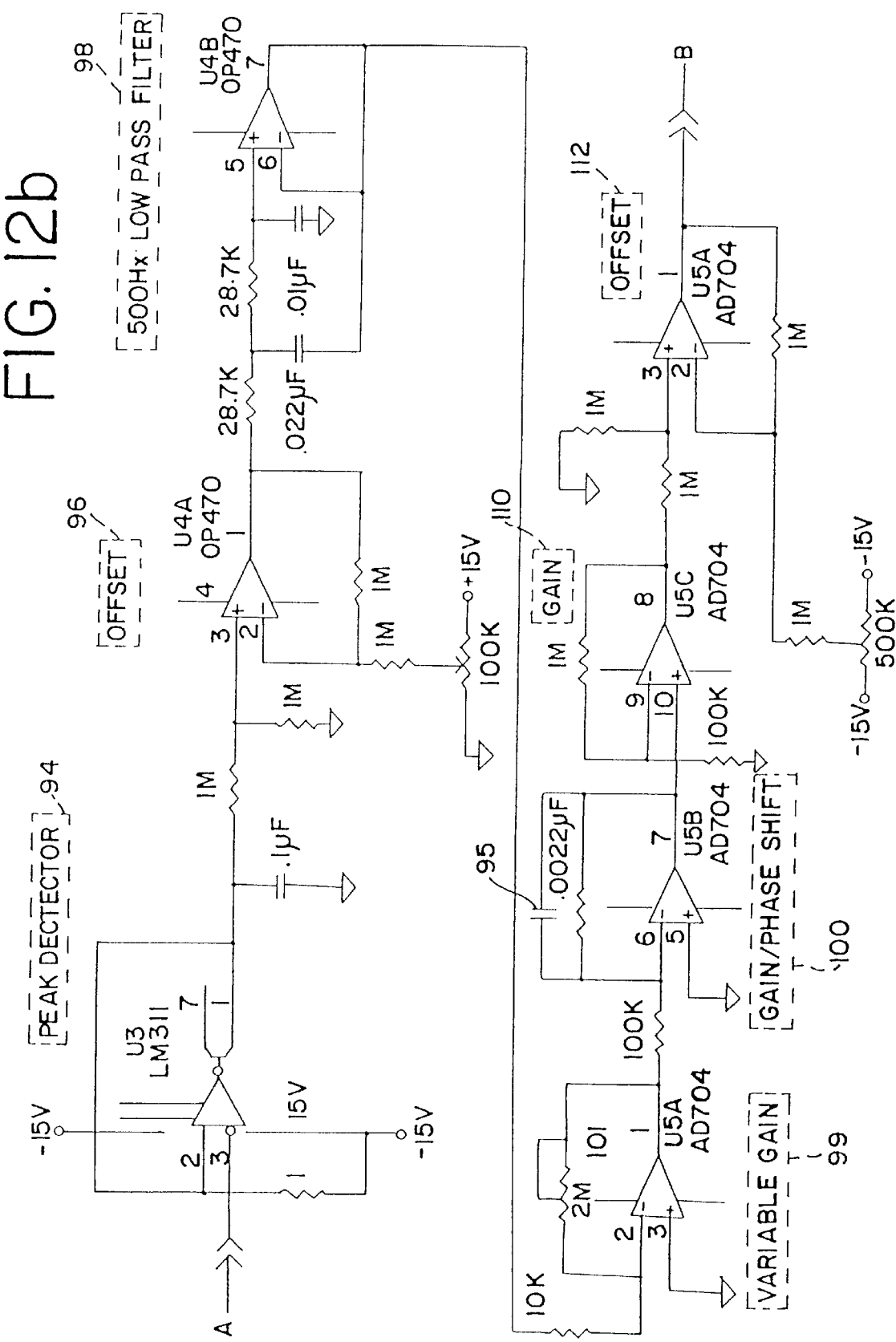
Figure 12C:
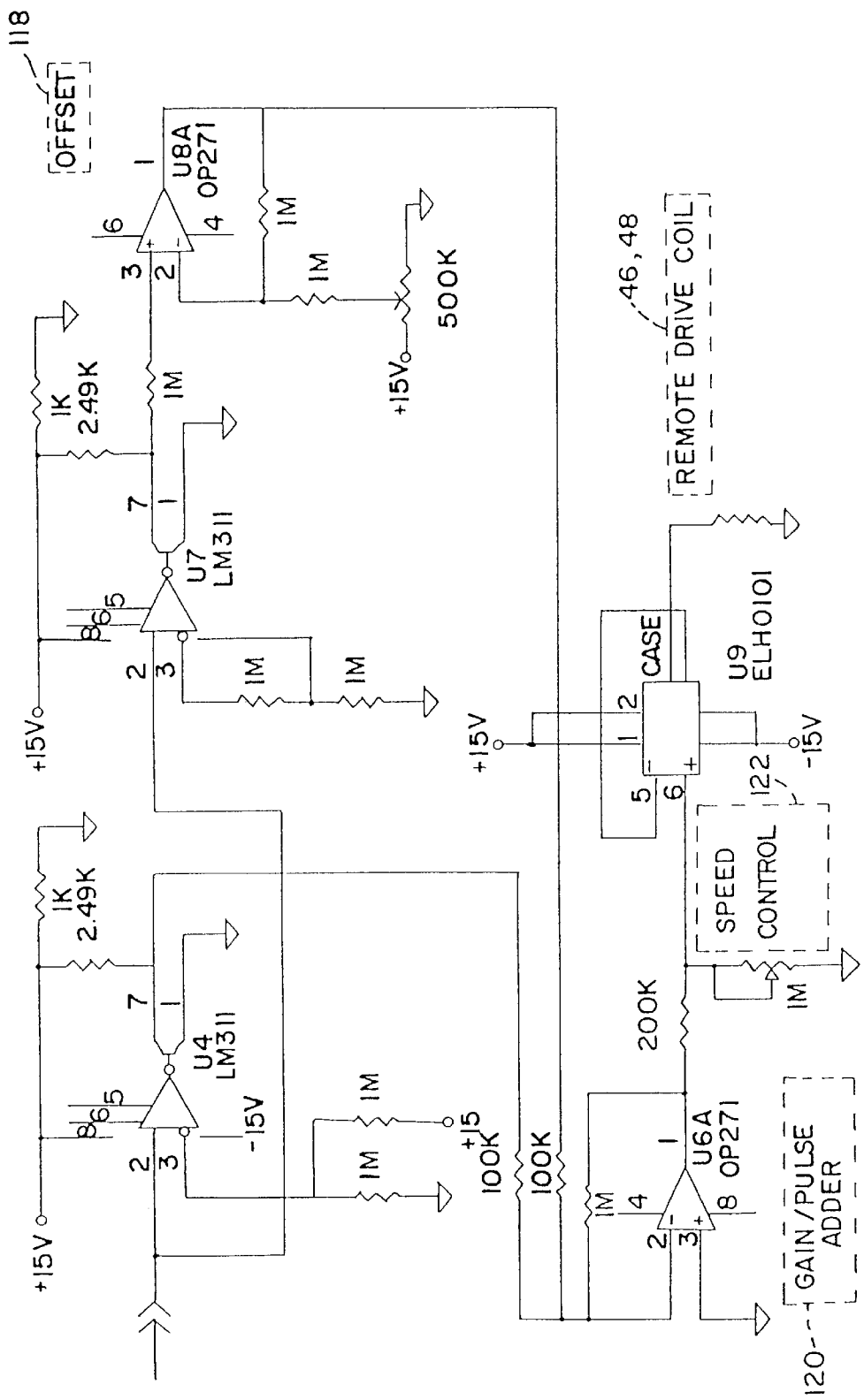

FIGS. 12*a*, 12*b* and 12*c* are schematic diagrams of another suitable circuit 30*b* for implementing the driving electronics 30 shown in FIG. 1. The circuit 30*b* is most advantageously used in connection with the motor 20*d* shown in FIGS. 8 and 9 in which cores 76, 78 are provided inside the driving coils 46, 48. Circuit 30*b* provides a pulsed current to the driving coils 46, 48 as shown by the wave-form in FIG. 14. The pulsed current from circuit 30*b* provides more off time and more current for a shorter period of time than the wave-form shown in FIG. 13. This is possible because the coils 46, 48 have sufficiently low inductance to respond to short bursts of current The high pulses of current are required to launch the magnet 42 away from the cores 76, 78.

Like circuit 30*a*, circuit 30*b* includes a conventional oscillator 80 which applies a 450 kHz sine wave through a buffer driver 84 and a resistor 85 to the sensor 60. The amplitude of the voltage across the sensor 60 varies in relation to the position of the magnet 42. The voltage across the sensor 60 is detected by the circuit 30*b* via leads 66 (shown in FIGS. 2–9) and applied to a gain stage 86 having a value of approximately 30. The output from gain stage 86 is applied to a high pass filter 88 which is set at approximately 100 kHz. The high pass filter 88 eliminates any DC noise levels generated in conductors 28.

Another gain stage 92 having a value of approximately 10 is applied to the output signal from the high pass filter 88 and fed into a peak detect circuit 94. The peak detect circuit 94 measures the amplitude of the signal from gain stage 92 and outputs a sine wave having an amplitude that corresponds to the proximity of the magnet 42 to the sensor 60. Also, the frequency of the signal from the peak detect circuit 94 corresponds to the period of the magnet's back and forth movements. For the disclosed embodiments, the frequency of the sine wave output from the peak detect circuit 94 is in the range from about 5 to about 500 Hertz. The peak detect output is applied to an offset circuit 96 to center it around zero, and then to a low pass filter 98 set at approximately 500 Hertz.

After the low pass filter 98, circuit 30*b* proceeds in a slightly different manner than circuit 30*a*. The output from the low pass filter 98 is fed to a variable gain circuit 99 and then to a gain/phase-shift circuit 100. The variable gain circuit 99 controls the width of the pulsed current to the driving coils 46, 48 by adjusting the variable resistor 101. The Gain/phase-shift circuit 100 includes a capacitor 95 which controls the timing of the current pulses to the driving coils 46, 48 by phase-shifting the pulses. For circuit 30b, the center point C is established by the center point between the pulses of current. Thus, the center point C can be adjusted by adjusting capacitor 95. If the load 22 is concentrated on one side of the magnet 42, it may be advantageous to establish the center point C closer to the load 22.

The signal from the gain/phase-shift circuit 100 is applied to another gain stage 110 and an offset 112. The output from the offset 112 is a sine wave which is applied to a positive pulse generator 114 and a negative pulse generator 116. The positive pulse generator 114 essentially ignores the negative values of its input wave-form and outputs a series of positive pulses corresponding to the peak positive values of the input. The negative pulse generator 116 essentially ignores the positive values of its input wave-form and outputs a series of negative pulses corresponding to the peak negative values of the input. An offset 118 adjusts any combined offset from the pulse generators 114, 116 down to zero.

A gain/pulse adder 120 adds the outputs from the positive pulse generator 114 and the negative pulse generator 116 (via offset 118). The output from the gain/pulse adder 120 is the applied through a speed control circuit 122 to the driving coils 46, 48 via leads 50, 52 and 54 (shown in FIGS. 2–9).

The speed control circuit 122 controls the speed or frequency of the magnet 42 by controlling the amplitude of the pulsed wave-form (shown in FIG. 14).

Turning now to FIGS. 15 to 23, particular applications of the in vivo mechanical energy sources will now be described. More specifically, the in vivo mechanical energy source will be described in relation to the perfusion pumps shown in FIGS. 15–20, and in relation to the balloon catheter and perfusion pump combinations shown in FIGS. 21–23.

Figure 15:
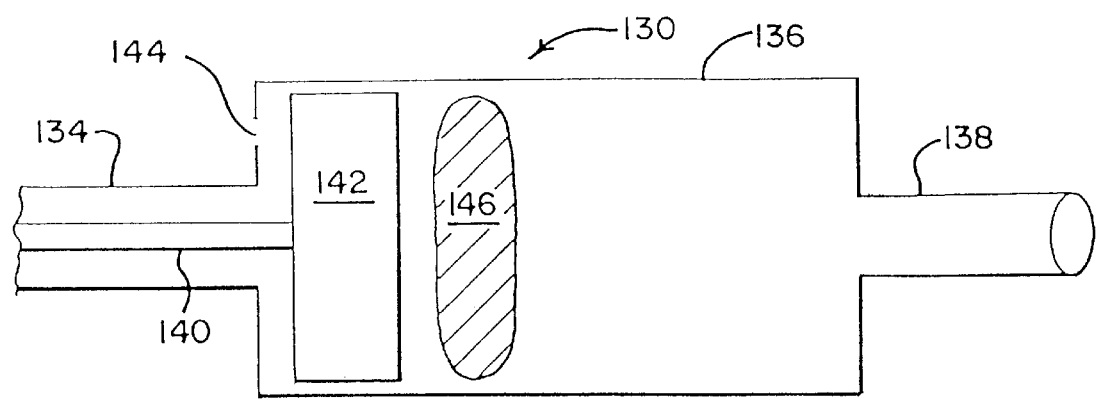
FIG. 15 illustrates an externally driven perfusion pump embodying features of the present invention.

FIG. 15 illustrates one embodiment of an externally driven pump 130 embodying features of the present invention. The externally driven pump 130 includes a large diameter tube 136. An elongated tubular shaft 134 is coupled to a proximal end of the large diameter tube 136, and another elongated tubular shaft 138 is coupled to a distal proximal end of the sheath layer 136. In general, the shaft 134 houses a push wire 140, the large diameter tube 136 houses a piston, and the distal shaft 138 acts as an exit tube for allowing fluid to be pumped from the pump device 130.

The push wire 140 is connected at its proximal end to an external reciprocating driver (not shown) A distal end of the push wire 140 is connected to a piston 142. The piston 142 is located inside one end of the large diameter tube 136. The piston 142 is disposed movably within the large diameter tube 136 such that the piston 142 may be reciprocated therein. An inlet hole 144 extends through the large diameter tube 136 to prevent a vacuum from forming behind the piston 142.

The pump 130 is operated by reciprocating the proximal end of the push wire 140 back and forth, thereby reciprocating the piston 142 back and forth. The piston 142 slidably covers and uncovers the inlet hole 146 extending through the large diameter tube 136. The piston 142 is reciprocated by a push wire 140 from a power source (not shown) located outside of the body. In this design, the piston 142 draws fluid into the large diameter tube 136 (as in a syringe) on the backstroke, thereby introducing proximal blood into the large diameter tube 136 when the piston 142 slides past the inlet hole 146. On the forward stroke, some blood is pushed back through the inlet hole 146 until it is covered by the piston 142. The remaining fluid is ejected through the exit shaft 138. This pump 130 has the advantage of a simple design that is capable of operating at high power and high frequency, limited only by the capacity of the outside power supply. The length of the pump 130 can be quite small, for example, 0.040 inches (as measured from approximately the proximal end of the large diameter tube 136 to approximately the distal end of the elongated tubular shaft 138), which is similar to the size of the micromotor-driven pumps (shown in FIGS. 16 to 18) but without the coil windings. Optionally, the pump 130 could be provided with coil windings described herein.

Turning now to FIG. 16, an in vivo mechanical-energy-source/perfusion-pump is illustrated in accordance with the present invention. In particular, FIG. 16 illustrates a single acting pump embodiment 150. The embodiment illustrated in FIG. 16 includes a large diameter tubular section 152 in fluid communication with a smaller diameter tubular section 154. The large diameter tubular section 152 generally houses the piston/mechanical-energy-source 156 and a valve 158. The smaller diameter tubular section 154 acts as an exit tube through which fluid is pumped from the single acting pump device 150.

The single acting pump device 150 further includes windings located around the large diameter tubular section 152. These windings include a pair of piston windings 160 and a pair of valve windings 162, located as illustrated in FIG. 16. The piston windings 160 are located in proximity to the piston magnet 156, and the valve windings 162 are located in proximity to the valve magnet 158. A set of tubular stops 164, 166 define the axial motion of the piston magnet 156, and another tubular stop 168, along with a shoulder portion 170, defines the axial movement of the valve magnet 158.

The piston magnet 156 and the valve magnet 158 illustrated in FIG. 16 are substantially the same as the reciprocating motors described earlier in the specification and illustrated in FIGS. 2–10. The two magnets 156, 158 are connected electrically in series but 180° out of phase (i.e., the two magnets always move in opposite directions). Because the micromotors are connected in series, only one set of electronics is used, and only two electrical wires extend from the motor windings (piston windings and valve windings) to the electronics. Thus, the two magnets automatically reciprocate in lock-step but 180° out of phase.

The piston magnet 156 is Preferably a solid cylindrical magnet which reciprocates within a main larger diameter polyimide tube 152 between two stops 164, 166. The stops 164, 166 are polyimide tubing sections which fit within the main polyimide tube 152. The solid magnet 156 is driven by two coils 160 wrapped around the outside diameter of the main polyimide tube 152. Preferably, the solid magnet 156 has a stroke of approximately 0.150 inches.

The valve magnet 158 is a tubular magnet which reciprocates between a tubular polyimide stop 168 and a shoulder 170 located within the same main polyimide tube as the piston magnet 156. It is driven by two sets of coils 162 wound around the outside diameter of the main polyimide tube 152. The main polyimide tube 152 is coated on its inside surface with a non-stick coating (for example, Teflon) to form a low friction interface with the magnets. An inlet hole 172 extends through the main polyimide tube 152 between the two sets of valve coils 162. When the valve magnet 158 moves to its proximal stop, it covers the inlet hole 172. When the valve magnet 158 moves to its distal stop, the inlet hole 172 is uncovered. The stroke of the valve magnet 158 is preferably about 0.030 inches, which is a sufficient length to cover and uncover the inlet hole 172.

When the piston magnet 156 is moving proximally, the valve magnet 158 is in its distal position, and the inlet hole 172 is open. Thus, during the proximal stroke of the piston 156, fluid is drawn into the main polyimide tube 152 through the inlet hole 172. A second path exists for fluid to enter the large diameter tubular section 152 through the hollow core of the tubular valve magnet 158, but this second path has relatively high resistance because fluid must travel through the relatively long and narrow exit tube (small diameter sheath 154). In the preferred embodiment, this exit tube 154 is approximately two inches long and approximately 0.020 inches in inside diameter. Thus, almost all of the fluid entering the large diameter sheath 152 during the proximal travel of the piston 156 enters via the inlet holes 172.

When the piston 156 moves distally, the valve magnet 158 moves to its proximal position, covering the inlet hole 172. The piston 156 then forces the fluid in the main tube 152 to travel through the hollow tubular valve magnet 158 and out through the exit tube (small diameter sheath 154). This cycle is repeated continuously, causing a stream of fluid to flow out of the exit tube.

Figure 18:
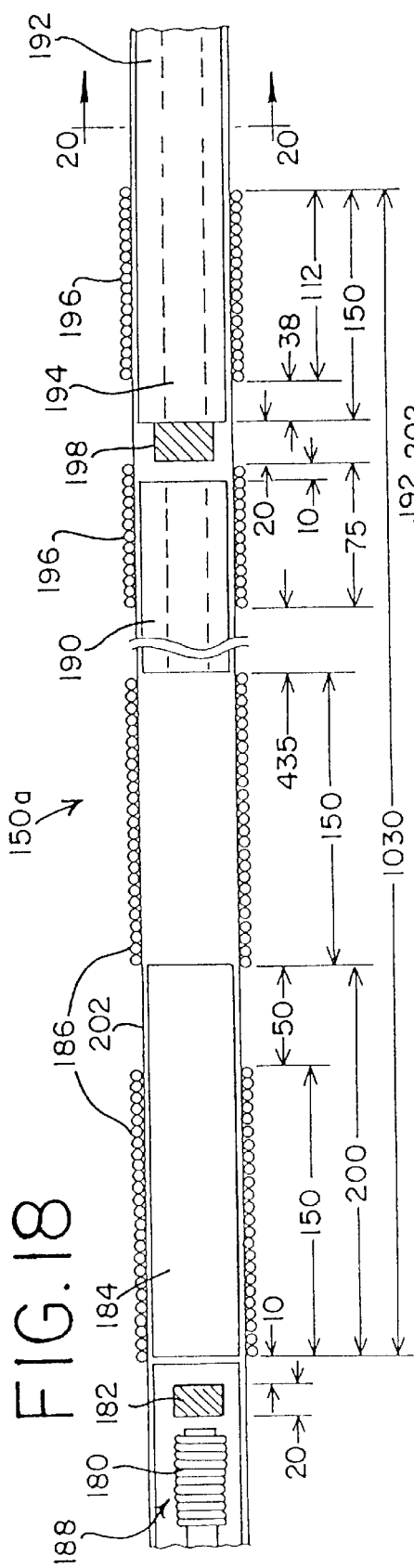
FIG. 18 illustrates a more detailed example of the single acting perfusion pump shown in FIG. 16.
Figure 19:
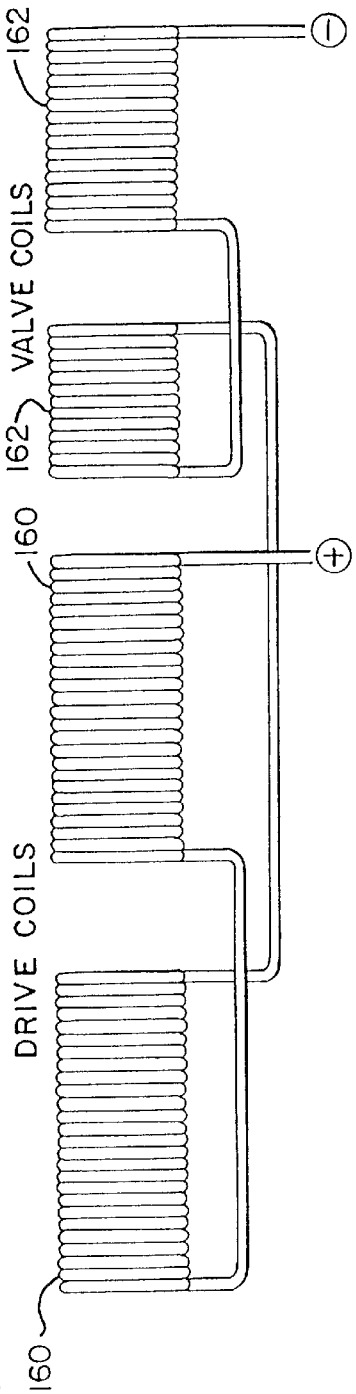
FIG. 19 illustrates the electrical connections between the drive coils and valve coils shown in FIGS. 16 and 18.

FIG. 19 illustrates the electrical connections that are made to the drive coils 160 and valve coils 162 illustrated generally in FIGS. 16 and 18. In general, both the drive coils 160 and the valve coils 162 are connected in series such that only two electrical connections must be made to access both sets of coils. As illustrated in FIG. 19, the distal end of the distal valve coil is connected to a negative current terminal while the proximal end of the distal valve coil is connected to the proximal end of the proximal valve coil. The distal end of the proximal valve coil is connected to the distal end of the proximal drive coil. The proximal end of the proximal drive coil is connected to the proximal end of the distal drive coil and the distal end of the distal drive coil is connected to a positive current terminal.

Using the electrical connection illustrated in FIG. 19, the in vivo energy source illustrated in FIGS. 16 and 18 reciprocates at about 90 cycles/second, and delivers about 20 ml/minute of water through an exit is tube which is about two inches long and about 0.020 inches in inside diameter. The in vivo-energy-source/pump generates about 3 watts of electrical power. Most of this power is lost as heat in the motor windings, and about 0.03 watts are converted into the pumping movements of the piston 156 and the valve 158. The windings are liquid cooled by the pumping fluid. The outside diameter of the pump windings is 0.060 inches, which is small enough for intravascular applications. In particular, the pump could reside proximal to the balloon of an angioplasty catheter, and pump blood to the distal side of the inflated balloon to prevent ischemia during the angioplasty procedure. Examples of a pump/balloon combination are illustrated in FIGS. 15–23. It is expected that a pump in accordance with the disclosed design(s), having an overall diameter of approximately 0.040 inches, would deliver approximately 20 ml/minute.

FIG. 18 illustrates at 150a a more detailed representation of the single acting pump represented schematically in FIG. 16. In particular, the pump 150a illustrated in FIG. 18 includes a sense coil 180 of the type described earlier in this disclosure, a vent 182, a pump magnet 184, drive coils 186, layered polyimide tubes 188, 190, 192, a valve magnet 194, valve coils 196, and two intake ports 198, 200. The sense coil 180, vent 182, pump magnet 184, layered polyimide tubes 188, 190, 192, intake port 198, 200, and valve magnet 194, are all housed inside a "size # 18" polyimide kink resistant tube 202. The drive coils 186 and valve coils 196 are wound around the outside of the # 18 polyimide kink resistant tube 202, which is preferably coated on its inner surface with a low friction material such as Teflon.

The sense coil 180 is wound around a layered polyimide tube 188, size #'s 19 and 20. The polyimide tube 202 that houses the major components of the pump 150a is a # 18 polyimide kink resistant tube having a Teflon inner-surface coating. The two polyimide tubes 190, 192 around the valve magnet 194 are layered polyimide tubes, size #'s 19, 20, 21, 22, and 24. The following table sets forth the inner diameter and outer diameter of the various sizes of polyimide tubing.

| POLYIMIDE TUBING DIMENSIONS | | |
| --- | --- | --- |
| Size # | Inner diameter | Outer diameter |
| 18 kink resistant | .0403 | .0463 |
| 19 | 0.359 | 0.379 |
| 20 | 0.320 | 0.340 |
| 21 | 0.285 | 0.305 |
| 22 | .0253 | .0273 |
| 24 | .0201 | .0221 |

The pump 150a is small enough to fit within a body vessel, and yet its in vivo energy source is powerful enough to supply the electrical power (at least about 1 watt, preferably about 3 watts) needed to run the pump 150a. The pump magnet 184 is preferably a cylinder measuring 200 mils by 38 mils. The drive coils 156 are preferably 42 gauge silver/ml, wound in three layers of 50 turns each, and having a length of approximately 150 mils. The distal-most of the pair of valve windings 196 is preferably 42 gauge silver/ml, wound in three layers of 25 turns each, and having a length of approximately 75 mils. The proximal-most of the pair of valve windings 196 is preferably 42 gauge silver/ml, wound in three layers of 37 turns each, and having a length of approximately 112 mils. The valve magnet 194 is preferably a cylinder measuring 150 mils by 38 mils, with an I.D. of 20 mils.

Figure 20:
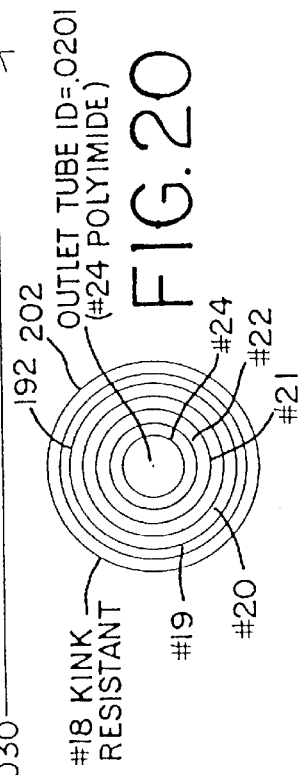
FIG. 20 is a cross-sectional view taken along line 20—20 in FIG. 18.

FIG. 20 illustrates a cross sectional detail taken along line 20—20 from FIG. 18. As illustrated in FIG. 20, the various polyimide tubing layers that make up the layered polyimide tube 192 are shown in terms of their relative sizes. The tubing layers are bonded together using loctite 460.

The dimensions of the pump components may be varied in order to achieve a desired output in a desired application. For example, a pump in accordance with the disclosed design can deliver 20 ml/minute with an overall diameter under 0.040 inches. Alternatively, a larger version of the same pump could be used to assist the heart in pumping blood to the body. The inlet to the pump would reside (or be attached to a tube which resides) in the left ventricle. The capacity of the larger pump would be proportional to the stroke volume, which can be constructed at least twenty times larger than the above-described embodiment. In addition, the larger pump would have a greatly increased electrical efficiency, so the pumping speeds would be increased for the same power output. Accordingly, outputs in excess of 1,000 ml/min can be achieved in a pump with approximately 0.14 inches in overall diameter.

FIG. 17 illustrates a double acting pump device 210. The pump 210 includes a sheath layer 151 formed from a large diameter portion 152, a small diameter portion 154, and a shoulder portion 170. The sheath layer 151 is housed substantially inside a flexible outer tube 208, which is preferably made from polyimide. A portion of the small diameter sheath 154 protrudes through a distal opening 230 in the outer tube 208 to allow fluid pumped through the small diameter sheath 154 to exit the pump 210. A suitable sealant is provided around the opening 230 to prevent fluid in the space 232 between the outer tube 208 and the sheath 151 from flowing out of the opening 230.

The double acting pump 210 is substantially the same in operation and size as the single acting pump 150 except for the addition of a second magnet valve 212, second valve windings 214, second valve stops 216, 218, an inlet 172a, and port 234, all of which are located proximal to the piston 156 Because of the additional components, the preferred length of the double acting pump 210 is approximately 2.5 inches. The inlets 172, 172a extend through both the sheath 151 and the outer tube 208. The additional valve 212 effectively doubles the pump's output. By adding the second valve, the piston pumps on the backstroke as well as on the forward stroke. Fluid is pumped over the coil windings in the space 232 between the outer tube 208 and the sheath 151, in through the port 234, and out through the small diameter sheath portion 154 which acts as an exit tube. The fluid flowing over the coils provides additional cooling, thereby increasing the efficiency of the micromotors, which can then achieve higher operating speeds. Thus, the output of the double acting micromotor pump 210 can be more than twice the output of the single acting pump 150.

Referring now to the details of the double acting pump 210 illustrated in FIG. 17, the large diameter tubular sheath 152 generally houses the piston/mechanical-energy-source 156, a first valve 158, and a second valve 212. Coil windings are wound around the large diameter tubular sheath 152 in the space 232 between the outer tube 208 and the large diameter sheath 152. These windings include piston windings 160, first valve windings 162, and second valve windings 214 located as illustrated in FIG. 17. The piston windings 160 are located in proximity to the piston magnet 156, the first valve windings 162 are located in proximity to the first valve magnet 158, and the third valve windings 214 are located in proximity to the second valve magnet 212. A is set of preferably tubular stops 164, 166 define the axial motion of the piston magnet 156. Another tubular stop 168 and a shoulder portion 170 define the axial movement of the first valve magnet 158. A set of tubular stops 216, 218 define the axial movement of the second valve magnet 158.

The piston magnet 156, the first valve magnet 158, and the second valve magnet 212 illustrated in FIG. 17 are substantially the same as the reciprocating motors described earlier in this disclosure. The three magnets 156, 158, 212 are connected electrically in series, but two of the magnets are 180° out of phase with the third magnet (i.e., two magnets move distally while the third magnet is moving proximally). Because the micromotors are connected in series, only one set of electronics is used, and only two electrical wires extend from the motor windings (piston windings and valve windings) to the electronics. Thus, the magnets automatically reciprocate in lock-step but with two of the magnets always 180° out of phase with the third magnet.

The piston magnet 156 is preferably a solid cylindrical magnet which reciprocates within the larger diameter polyimide tube 152 between two stops 164, 166. The stops 164, 166 are polyimide tubing sections which fit within the main polyimide tube 152. The solid magnet 156 is driven by two coils 160 wrapped around the outside diameter of the main polyimide tube 152. Preferably, the solid magnet 156 has a stroke of approximately 0.150 inches.

The first valve magnet 158 is a tubular magnet which reciprocates between a tubular polyimide stop 168 and a shoulder 170 located within the same large diameter tube 152 as the piston magnet. It is driven by two sets of coils 162 wound around the outside diameter of the main polyimide tube 152. This main polyimide tube 152 within which the magnets reciprocate is coated on its inside surface with a non-stick coating (for example, Teflon) to form a low friction interface with the magnets. An inlet hole 172 is in the main polyimide tube 152 between the two sets of valve coils 162. When the first valve magnet 158 moves to its proximal stop, it covers the inlet hole 172. When the first valve magnet 158 moves to its distal stop, the inlet hole 172 is clear and open. Preferably, the stroke of the first valve magnet 158 is approximately 0.030 inches, which is a sufficient length to cover and uncover the inlet hole 172.

The second valve magnet 212 is also a tubular magnet substantially identical to the first valve magnet 158. The second valve magnet 212 reciprocates between two polyimide tube stops 216 and 218 located within the same large diameter tube 152 as the piston magnet 156. It is driven by two sets of coils 214 wound around the outside diameter of the main polyimide tube 152. Another inlet hole 172a is in the main polyimide tube 152 between the two sets of valve coils 214. When the second valve magnet 212 moves to its proximal stop, it covers the inlet hole 172a. When the second valve magnet 212 moves to its distal stop, the inlet hole 172a is uncovered. Preferably, the stroke of the second valve magnet 212 is 0.030 inches, which is a sufficient length to both cover and uncover the inlet hole 172a.

The solid piston magnet 156 effectively divides the space inside the sheath layer 151 of the double acting pump 210 into a proximal chamber 236 and a distal chamber 238. When the piston magnet 156 is moving proximally, the first valve magnet 158 is in its distal position, and the inlet hole 172 is open. Thus, during the proximal stroke of the piston 156, fluid is drawn into the distal chamber 238 of the main polyimide tube 152 through inlet hole 172. Another path exists for fluid to enter through the distal end of the smaller diameter sheath 154 and the hollow core of the tubular first valve magnet 158, but this second path has relatively high resistance because fluid must travel through the entire length of the relatively long and narrow small diameter sheath 154. Thus, almost all of the fluid entering the distal chamber 238 of the main tube 152 during the proximal travel of the piston 156 enters via the inlet hole 172. In the preferred embodiment, the small diameter sheath 154 is approximately 10 inches long, and the port 234 is positioned approximately 2 inches from the distal end of the small diameter sheath 154.

When the piston 156 moves distally (as illustrated in FIG. 17), the first valve magnet 158 moves to its proximal position, covering the inlet hole 172. The distal stroke of the piston 156 forces the fluid in the distal chamber 238 of the main tube 152 to travel through the hollow tubular valve magnet 158 and out of the exit tube (small diameter sheath 154). This cycle is repeated continuously, causing a stream of fluid to flow out of the exit tube.

The port 234 extends through a sidewall of the small diameter sheath 154 at a point that is near the distal end of the sheath 154, thus presenting a path of considerably more resistance to backflow than the open distal end of the sheath 154. Accordingly, substantially all of the fluid traveling distally through the small diameter sheath 154 exits through the open distal end of the sheath 154 instead of the port 234.

When the piston magnet 156 is moving proximally, the second valve magnet 212 is in its proximal position, covering the inlet hole 172a. The proximal stroke of the piston 156 forces the fluid in the proximal chamber 236 of the main tube 152 to travel through a prescribed pathway to the exit tube (small diameter sheath 154). The prescribed pathway is through the tubular second valve magnet 212, out of the distal end of the large diameter sheath 152, distally through the space 232 between the sheath 151 and the outer tube 208, through the port 234 located on the small diameter sheath 154, and out of the exit tube (small diameter sheath 154). Because the port 234 extends through a sidewall of the small diameter sheath 154 close to the distal end of the sheath 154, it presents a path of considerably more resistance to backflow than the open distal end of the sheath 154. Accordingly, substantially all of the fluid traveling distally through the small diameter sheath 154 exits through the open distal end of the sheath 154 instead of flowing proximally into the sheath 154.

When the piston 156 moves distally (as illustrated in FIG. 17), the second valve magnet 212 moves to its distal position, and the inlet hole 172a is uncovered. Thus, during the distal stroke of the piston 156, fluid is drawn into the proximal chamber 236 of the main polyimide tube 152 through the inlet hole 172a and the tubular second valve magnet 212.

Figure 21:
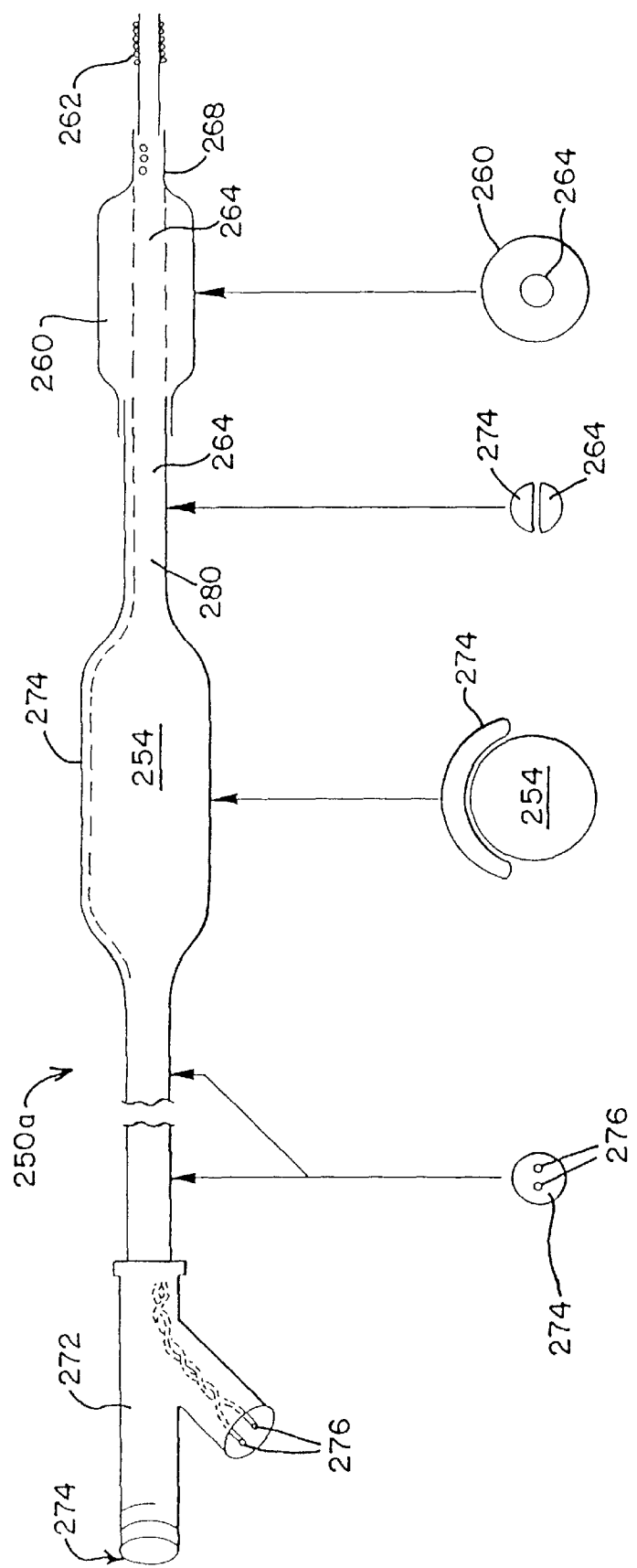
FIG. 21 illustrates a balloon/pump/energy-source catheter embodying the present invention.
Figure 22:
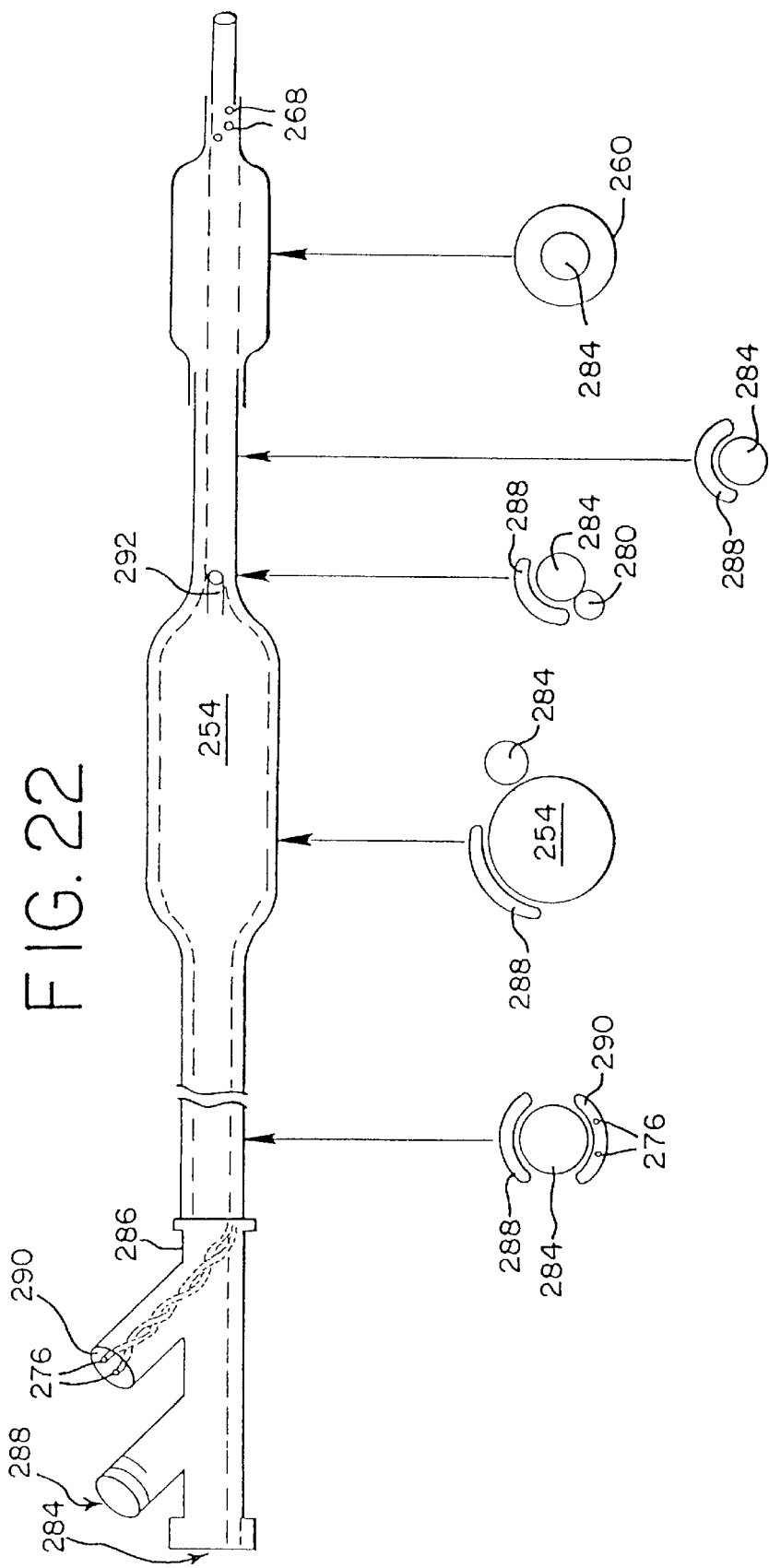
FIG. 22 illustrates another balloon/pump/energy-source catheter embodying the present invention.
Figure 23:
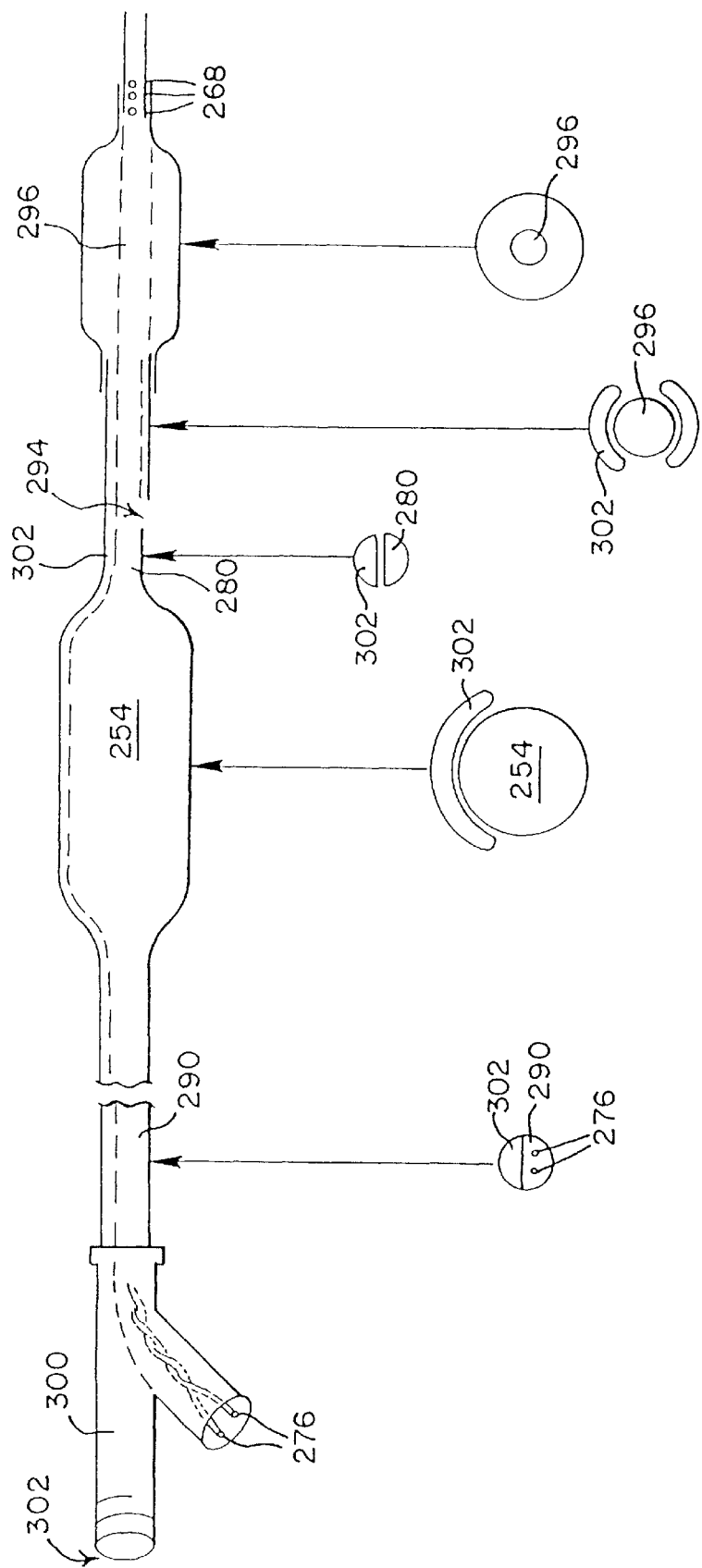
FIG. 23 illustrates yet another balloon/pump/energy-source catheter embodying the present invention.

FIGS. 21 to 23 illustrate further embodiments of the present invention in which any one of the above-described pumps is utilized with a PTCA balloon catheter. The illustrated catheters 250a, 250b, 250c, are preferably used in coronary angioplasty procedures, but may also be used in a other percutaneous transluminal treatments, such as cerebral or peripheral angioplasties. The general objective of these treatments is to open obstructions or lesions within a body vessel such as a blood vessel. For example, in PTCA, a guide catheter (not shown) is introduced at an appropriate location in the patient's body and routed through the vascular system into the aorta and coronary orifice. A thin and relatively flexible guide wire is advanced through the guide catheter to the arteries, and then steered into side branches (if necessary) to access the obstruction. Once the guide wire has established a path across the obstruction, an "over-the-wire" dilatation balloon catheter is passed over the proximal end of the guide wire until the balloon is adjacent the obstruction. The balloon is then inflated by introducing a fluid into the balloon through an inflation lumen in the catheter. The inflated balloon expands against the blockage to dilate the obstructed blood vessel. Another type of balloon catheter known as "fixed-wire," eliminates the need for a separate guide wire by attaching a short flexible guide wire to the distal end of the catheter.

The catheter 250a illustrated in FIG. 21 includes an in vivo pump 254 adjacent an inflatable balloon 260 and spring-tipped fixed wire 262. The balloon 260 may be used to perform conventional balloon angioplasty on an obstructed region of a body lumen. The pump 254 may be used to draw fluid inside the catheter 250a through an inlet (not shown), and then pump that fluid through a perfusion lumen 264 that extends through the balloon 260 (when inflated) and feeds to outlet or perfusion holes 268 located just distally from the balloon 260. The pump 254 is preferably any one of the pumps described earlier herein. In general, these pumps include a mechanical energy source, preferably a miniaturized energy source that is small enough to fit within the catheter, yet powerful enough to generate about 1 watt of power and deliver about 0.01 watts of power.

The proximal end of the catheter 250a is coupled to a conventional manifold 272 which couples inflation fluid to an inflation lumen 274 extending along the length of the catheter 250a, and also couples lead wires 276 (preferably AW6#38 silver) through the same inflation lumen 274 to the pump 254. The pump 254 is located at a distal end of the catheter 250a, and may be any one of the pump designs described earlier herein. The inflation lumen 274 extends over, around and past the pump 254, and on to the balloon 260. The pump's fluid exit tube 280 (of the type described earlier herein) feeds into a perfusion lumen 264. When inflated, the balloon 260 forms a tube having a substantially open central region, and the perfusion lumen 264 extends through this central region of the inflated balloon 260. Perfusion holes 268 extend through the catheter 250a at a point just distal of the balloon 260, and provide a path for fluid pumped through the perfusion lumen 264 to leave the catheter 250a.

The catheter 250b illustrated in FIG. 22 is substantially the same as the catheter 250a shown in FIG. 21 except the catheter 250b of FIG. 22 is an over-the-wire type catheter having a guide wire lumen 280 extending through the length of the catheter 250b.

The proximal end of the catheter 250b is coupled to a conventional manifold 286 which couples inflation fluid to an inflation lumen 288 extending along the length of the catheter 250b, and also couples lead wires 276 (preferably AW6#38 silver) through a separate lumen 290 leading to the pump 254. Also, the manifold 286 feeds into the guide wire lumen 284.

The pump 254 is located at a distal end of the catheter 250b, and may be any one of the pump designs described earlier herein. The inflation lumen 288 extends over, around and past the pump 254, and on to the balloon 260. The guide wire lumen 284 also extends over, around, and past the pump 254, and on to the balloon 260. The pump's fluid exit tube 280 (of the type described earlier herein) feeds into the guide wire lumen 284 at a point proximal of the balloon 260. Thus the guide wire lumen 284 also serves as a perfusion lumen. When inflated, the balloon 260 forms a tube having a substantially open central region, and the perfusion/guide wire lumen 284 extends through this central region of the inflated balloon. Perfusion holes 268 extend through the catheter 250b at a point just distal of the balloon 260, and provide a path for fluid pumped through the perfusion/guide wire lumen 284 to leave the catheter 250b.

To allow sufficient blood flow through the perfusion/guide wire lumen 284, the guide wire 292 is preferably pulled back near the pump 254 as illustrated. Optionally a separate perfusion lumen could be provided at the expense of increasing the outer diameter of the catheter. Also, the guide wire lumen 284 could be enlarged to allow blood to perfuse in the space between the guide wire and the inner lumen wall, also at the expense of increasing the outer diameter of the catheter 250b.

The catheter 250c illustrated in FIG. 23 is substantially the same as the catheter 250b shown in FIG. 22 except the guide wire entry point 294 is located between the pump 254 and the balloon 260, thus the guide wire lumen 296 extends through only the distal end of the catheter 250c.

The proximal end of the catheter 250c is coupled to a conventional manifold 300 which couples inflation fluid to an inflation lumen 302 extending along the length of the catheter 250c, and also couples lead wires 276 (preferably 38 gauge silver insulated) through a separate lumen 290 leading to the pump 254.

The pump 254 is located at a distal end of the catheter 250c, and may be any one of the pump designs described earlier herein. The inflation lumen 302 extends over, around and past the pump 254, and on to the balloon 260. The pump's fluid exit tube 280 (of the type described earlier herein) feeds into the guide wire lumen 296 at a point proximal of the balloon 260. Thus, at the distal end of the catheter, 250a, the guide wire lumen 296 also serves a perfusion lumen. When inflated, the balloon 260 forms a tube having a substantially open central region, and the perfusion/guide wire lumen 296 extends through this central region of the inflated balloon 260. Perfusion holes 268 extend through the catheter 250c at a point just distal of the balloon 260, and provide a path for fluid pumped through the perfusion/guide wire lumen 296 to leave the catheter 260.

To allow sufficient blood flow through the perfusion/guide wire lumen 296, the guide wire (not shown) is preferably pulled back near the balloon 260. Optionally, the perfusion/guide wire lumen 296 could be enlarged to allow blood to perfuse in the space between the guide wire and the inner lumen wall, thus increasing the outer diameter of the catheter 250c.

While the above described embodiments of the invention are preferred, those skilled in this art will recognize modifications of structure, arrangement, composition and the like which do not part from the true scope of the invention. The scope of the invention is defined by the appended claims, and all devices and/or methods that fall within the meaning of the claims, either literally or by equivalents, are intended to be embraced therein.

What is claimed is:

1. A system for performing a vascular therapy comprising:

a catheter having a distal end and an axis;

a micromotor attached to the catheter;

a power source coupled to the catheter but distant from the distal end of the catheter; and a therapeutic device actuated by the micromotor and connected to the catheter adjacent the distal end of the catheter and actuated by the micromotor.

2. The micromotor of claim 1 wherein the therapeutic device further comprises a piston actuated by the motor.

3. The piston of claim 2 wherein the piston reciprocates along the axis of the catheter.

4. The system for performing a vascular therapy of claim 1 wherein the therapeutic device is a balloon catheter.

5. The system for performing a vascular therapy of claim 1 wherein the therapeutic device is a atherectomy device.

6. The system for performing a vascular therapy of claim 1 wherein the therapeutic device is a dottering device.

7. The system for performing a vascular therapy of claim 1 wherein the therapeutic device is a perfusion catheter.

8. The micromotor of claim 1 comprising reciprocating magnets aligned with the axis of the catheter.

9. The power source of claim 1 coupled to the micromotor via electrical leads.

10. An in-vivo therapy device comprising:

an elongate member having a distal end;

a motor mounted near the distal end of the elongate member;

a power source coupled to the motor; and a therapeutic device mounted on the elongate member and actuated by the motor.

11. The in-vivo therapy device of claim 10 wherein the power source is coupled to the motor via electrical lead leads.

12. The in-vivo therapy device of claim 10 wherein the therapeutic device comprises a balloon.

13. The in-vivo therapy device of claim 11 wherein the therapeutic device comprises an atherectomy device.

14. The in-vivo therapy device of claim 11 wherein the therapeutic device comprises a dottering device.

15. The in-vivo therapy device of claim 11 wherein the therapeutic device comprises a perfusion device.

16. A vascular therapy device comprising:

a catheter having a distal end;

a therapeutic device attached to the distal end of the catheter; and a means for actuating the therapeutic device.

17. The vascular therapy device of claim 16 wherein the means for actuating the therapeutic device comprises a micromotor.

18. The vascular therapy device of claim 17 wherein the means for actuating the therapeutic device further comprises a power source coupled to the micromotor.

19. The vascular therapy device of claim 18 wherein the power source is located near a proximal end of the catheter.

20. The vascular therapy device of claim 18 wherein the power source is coupled to the micromotor via electrical leads.

21. The vascular therapy device of claim 17 wherein the micromotor is located adjacent the distal end of the catheter.

22. The vascular therapy device of claim 16 wherein the therapeutic device is selected from the group consisting of balloons, atherectomy devices, dottering devices, and perfusion devices.

* * * * *